US008765788B2

(12) United States Patent
Powers et al.

(10) Patent No.: US 8,765,788 B2
(45) Date of Patent: Jul. 1, 2014

(54) TRICYCLIC INHIBITORS OF HYDROXYSTEROID DEHYDROGENASES

(75) Inventors: Jay P. Powers, Pacifica, CA (US); Daqing Sun, Foster City, CA (US); Xuelei Yan, Foster City, CA (US); Lisa Julian, Champaign, IL (US); Felix Gonzalez Lopez De Turiso, San Mateo, CA (US)

(73) Assignee: Amgen Inc., Thousand Oaks, CA (US)

( * ) Notice: Subject to any disclaimer, the term of this patent is extended or adjusted under 35 U.S.C. 154(b) by 198 days.

(21) Appl. No.: 12/664,137

(22) PCT Filed: Jun. 11, 2008

(86) PCT No.: PCT/US2008/007269
§ 371 (c)(1),
(2), (4) Date: Jun. 23, 2010

(87) PCT Pub. No.: WO2008/156601
PCT Pub. Date: Dec. 24, 2008

(65) Prior Publication Data
US 2010/0280073 A1    Nov. 4, 2010

Related U.S. Application Data

(60) Provisional application No. 60/929,132, filed on Jun. 14, 2007.

(51) Int. Cl.
*A61K 31/445* (2006.01)
*A61K 31/425* (2006.01)
*A61K 31/42* (2006.01)

(52) U.S. Cl.
USPC ............ 514/326; 514/365; 514/374; 514/378

(58) Field of Classification Search
None
See application file for complete search history.

(56) References Cited

FOREIGN PATENT DOCUMENTS

| JP | 11049762 A | 2/1999 | |
|---|---|---|---|
| WO | WO 96/29330 A1 | 9/1996 | |
| WO | WO 01/27094 A1 | 4/2001 | |
| WO | WO 02/064136 | * 8/2002 | ............ A61K 31/42 |
| WO | WO 2005/116002 | 12/2005 | |
| WO | WO 2006/025517 | * 3/2006 | ......... A61K 31/4465 |
| WO | WO 2007/061661 | 5/2007 | |

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Stella et al (Prodrugs: Challenges and Rewards, Part 1, 2007).*
CAS RN 221212-15-3 (entered into STN Apr. 15, 1999).*
CAS RN 180200-67-3 (entered into STN Aug. 29, 1996).*
Hashimoto, et al., "4-(4-Cycloalkyl/aryl-oxazol-5-yl)benzenesulfonamides as Selective Cyclooxygenase-2 Inhibitors: Enhancement of the Selectivity by Introduction of a Fluorine Atom and Identification of a Potent, Highly Selective, and Orally Active COX-2 Inhibitor JTE-522," J. Med. Chem., 2002, 45:1511-1517.
Isomura, et al., "Synthesis and Anti-inflammatory Activity of 2,6-Di-tert-butylphenols with a Heterocyclic Group at the 4-Position. III.," Chem. Pharm. Bull., 1984, 32(1):152-165.
Silvestre, et al., "JTE-522 Antiinflammatory Cyclooxygenase-2 Inhibitor," Drugs of the Future, 1998, 23(6):598-601.
Robichaud et al., "beta-Substituted cyclohexanecarboxamide catheps in K inhibitors: Modification of the 1, 2-disubstituted aromatic core", Bioorganic & Medicinal Chemistry Letters, vol. 17, No. 11, 2007, pp. 3146-3151.
International Search Report of the corresponding application PCT/US2008/007269, dated Sep. 16, 2008. (3 pgs.).

* cited by examiner

*Primary Examiner* — Craig Ricci
(74) *Attorney, Agent, or Firm* — Elsa D. Lemoine

(57) ABSTRACT

The present invention provides tricyclic compounds according to formula (I): (I) where $R^1$, $R^2$, $R^3$, W, X, Y, Z, m, n, and p are as defined in the description; as well as pharmaceutical compositions comprising the same, methods of use of the compounds and compositions of the invention for the treatment of conditions associated with hydroxysteroid dehydrogenases (e.g., 11-HSD1), and the use of the compounds of the invention in the preparation of medicaments for the treatment of hydroxysteroid dehydrogenase-associated conditions.

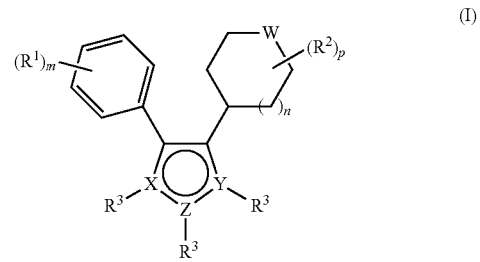

4 Claims, No Drawings

TRICYCLIC INHIBITORS OF HYDROXYSTEROID DEHYDROGENASES

BACKGROUND OF THE INVENTION

The present invention is generally directed to novel compounds, compositions, and the use of either in methods for modulating hydroxysteroid dehydrogenases, such as 11β-HSD1, and for treating or preventing diseases associated with the modulation of hydroxysteroid dehydrogenases, such as diabetes and obesity. The methods comprise the administration, to a patient in need thereof, of a therapeutically effective amount of a tricyclic compound. Novel tricyclic compounds or pharmaceutically acceptable salts, solvates, stereoisomers, or prodrugs thereof are presented herein.

Hydroxysteroid dehydrogenases (HSDs) regulate the occupancy and activation of steroid hormone receptors by converting steroid hormones into their inactive metabolites. For a recent review, see Nobel et al., Eur. J. Biochem. 2001, 268:4113-4125.

There exist numerous classes of HSDs. The 11-beta-hydroxysteroid dehydrogenases (11β-HSDs) catalyze the interconversion of active glucocorticoids (such as cortisol and corticosterone), and their inert forms (such as cortisone and 11-dehydrocorticosterone). The isoform 11-beta-hydroxysteroid dehydrogenase type 1 (11β-HSD1) is expressed in liver, adipose tissue, skeletal muscle, bone, brain, lung, and other glucocorticoid tissues and is a potential target for therapy directed at numerous disorders that may be ameliorated by reduction of glucocorticoid action, such as diabetes, obesity, and age-related cognitive dysfunction. Seckl et al., Endocrinology 2001, 142:1371-1376.

It is well known that glucocorticoids play a central role in the development of diabetes and that glucocorticoids enable the effect of glucagon on the liver. Long et al., J. Exp. Med. 1936, 63:465-490; and Houssay, Endocrinology 1942, 30:884-892. In addition, it has been well substantiated that 11β-HSD1 plays an important role in the regulation of local glucocorticoid effect and of glucose production in the liver. Jamieson et al., J. Endocrinol. 2000, 165:685-692.

Furthermore, the hypothesized mechanism of action of HSDs in the treatment of diabetes has been supported by various experiments conducted in mice and rats. These studies showed that the mRNA levels and activities of two key enzymes in hepatic glucose production, phosphoenolpyruvate carboxykinase (PEPCK) and glucose-6-phosphatase (G6Pase), were reduced upon administration of HSD inhibitors. In addition, blood glucose levels and hepatic glucose production were shown to be reduced in 11β-HSD1 knockout mice. Additional data gathered using this murine knockout model also confirm that inhibition of 11β-HSD1 will not cause hypoglycemia, since the basal levels of PEPCK and G6 Pase are regulated independently of glucocorticoids. Kotelevtsev et al., Proc. Natl. Acad. Sci. USA 1997, 94:14924-14929.

HSDs also play a role in obesity. Obesity is an important factor in Syndrome X as well as type II (non-insulin-dependent) diabetes, and omental fat appears to be of central importance in the development of both of these diseases, as abdominal obesity has been linked with glucose intolerance, hyperinsulinemia, hypertriglyceridemia, and other factors of Syndrome X (e.g., raised blood pressure, decreased levels of HDL, and increased levels of VLDL). Montague et al., Diabetes 2000, 49:883-888. It has also been reported that inhibition of the 11β-HSDs in pre-adipocytes (stromal cells) resulted in a decreased rate of differentiation into adipocytes. This is predicted to result in diminished expansion (possibly reduction) of the omental fat depot, which may lead to reduced central obesity. Bujalska et al., Lancet 1997, 349: 1210-1213.

Inhibition of 11β-HSD1 in mature adipocytes is expected to attenuate secretion of the plasminogen activator inhibitor 1 (PAI-1), which is an independent cardiovascular risk factor, as reported in Halleux et al., J. Clin. Endocrinol. Metab. 1999, 84:4097-4105. In addition, a correlation has been shown to exist between glucocorticoid activity and certain cardiovascular risk factors. This suggests that a reduction of the glucocorticoid effects would be beneficial in the treatment or prevention of certain cardiovascular diseases. Walker et al., Hypertension 1998, 31:891-895; and Fraser et al., Hypertension 1999, 33:1364-1368.

HSDs have also been implicated in the process of appetite control and therefore are believed to play an additional role in weight-related disorders. It is known that adrenalectomy attenuates the effect of fasting to increase both food intake and hypothalamic neuropeptide Y expression. This suggests that glucocorticoids play a role in promoting food intake and that inhibition of 11β-HSD1 in the brain may increase satiety, thus resulting in decreased food intake. Woods et al., Science 1998, 280:1378-1383.

Another possible therapeutic effect associated with modulation of HSDs is that which is related to various pancreatic aliments. It is reported that inhibition of 11β-HSD1 in murine pancreatic β-cells results in increased insulin secretion. Davani et al., J. Biol. Chem. 2000, 275:34841-34844. This follows from the discovery that glucocorticoids were previously found to be responsible for reduced pancreatic insulin release in vivo. Billaudel et al., Horm. Metab. Res. 1979, 11:555-560. Thus, it is suggested that inhibition of 11β-HSD1 would yield other beneficial effects in the treatment of diabetes other than the predicted effects on the liver and fat reduction.

11β-HSD1 also regulates glucocorticoid activity in the brain and thus contributes to neurotoxicity. Rajan et al., Neuroscience 1996, 16:65-70; and Seckl et al., Neuroendocrinol. 2000, 18:49-99. Stress and/or glucocorticoids are known to influence cognitive function (de Quervain et al., Nature 1998, 394:787-790), and unpublished results indicate significant memory improvement in rats treated with a non-specific 11β-HSD inhibitor. These reports, in addition to the known effects of glucocorticoids in the brain, suggest that inhibiting HSDs in the brain may have a positive therapeutic effect against anxiety and related conditions. Tronche et al., Nature Genetics 1999, 23:99-103. 11β-HSD1 reactivates 11-DHC to corticosterone in hippocampal cells and can potentiate kinase neurotoxicity, resulting in age-related learning impairments. Therefore, selective inhibitors of 11β-HSD1 are believed to protect against decline of hippocampal function with age. Yau et al., Proc Natl. Acad. Sci. USA 2001, 98:4716-4721. Thus, it has been hypothesized that inhibition of 11β-HSD1 in the human brain would protect against deleterious glucocorticoid-mediated effects on neuronal function, such as cognitive impairment, depression, and increased appetite.

HSDs are believed to play a role in immunomodulation based on the general perception that glucocorticoids suppress the immune system. There is known to be a dynamic interaction between the immune system and the HPA (hypothalamo-pituitary-adrenal) axis (Rook, Baillier's Clin. Endocrinol. Metab. 2000, 13:576-581), and glucocorticoids help balance cell-mediated responses and humoral responses. Increased glucocorticoid activity, which may be induced by stress, is associated with a humoral response and as such, inhibition of 11β-HSD1 may result in shifting the response towards a cell-based reaction. In certain disease states, such as tuberculosis, leprosy, and psoriasis, the immune reaction is typically biased toward a humoral response when a cell-based response might be more appropriate. Inhibition of 11β-HSD1 is being studied for use to direct a cell-based response in these instances. Mason, Immunology Today 1991, 12:57-60. It follows then that an alternative utility of 11β-HSD1 inhibition would be to bolster a temporal immune response in association with immunization to ensure that a cell-based response would be obtained.

Recent reports suggest that the levels of glucocorticoid target receptors and HSDs are connected with the risks of developing glaucoma. Stokes et al., Invest. Opthalmol. 2000, 41:1629-1638. Further, a connection between inhibition of 11β-HSD1 and lowering of intraocular pressure was reported. Walker et al., poster P3-698 at the Endocrine Society meeting Jun. 12-15, 1999, San Diego. It was shown that administration of the nonspecific 11β-HSD1 inhibitor, carbenoxolone, resulted in reduction of intraocular pressure by 20% in normal patients. In the eye, 11β-HSD1 is expressed exclusively in the basal cells of the corneal epithelium, the non-pigmented epithelialium of the cornea (the site of aqueous production), ciliary muscle, and the sphincter and dilator muscles of the iris. In contrast, the distant isoenzyme 11β-hydroxysteroid dehydrogenase type 2 ("11β-HSD2") is highly expressed in the non-pigmented ciliary epithelium and corneal endothelium. No HSDs have been found at the trabecular meshwork, which is the site of drainage. Therefore, 11β-HSD1 is suggested to have a role in aqueous production.

Glucocorticoids also play an essential role in skeletal development and function, but are detrimental to such development and function when present in excess. Glucocorticoid-induced bone loss is partially derived from suppression of osteoblast proliferation and collagen synthesis. Kim et al., J. Endocrinol. 1999, 162:371-379. It has been reported that the detrimental effects of glucocorticoids on bone nodule formation can be lessened by administration of carbenoxolone, which is a non-specific 11β-HSD1 inhibitor. Bellows et al., Bone 1998, 23:119-125. Additional reports suggest that 11β-HSD1 may be responsible for providing increased levels of active glucocorticoid in osteoclasts, and thus in augmenting bone resorption. Cooper et al., Bone 2000, 27:375-381. This data suggests that inhibition of 11β-HSD1 may have beneficial effects against osteoporosis via one or more mechanisms which may act in parallel.

It is known that bile acids inhibit 11β-HSD2 and that such inhibition results in a shift in the cortisol/cortisone equilibrium in the favor of cortisol. Quattropani et al., J. Clin. Invest. November 2001, 108:1299-305. A reduction in the hepatic activity of 11β-HSD2 is therefore predicted to reverse the cortisol/cortisone equilibrium to favor cortisone, which could provide therapeutic benefit in diseases such as hypertension.

The various isozymes of the 17-beta-hydroxysteroid dehydrogenases (17β-HSDs) bind to androgen receptors or estrogen receptors and catalyze the interconversion of various sex hormones, including estradiol/estrone and testosterone/androstenedione. To date, six isozymes have been identified in humans and are expressed in various human tissues, including endometrial tissue, breast tissue, colon tissue, and the testes. 17-beta-Hydroxysteroid dehydrogenase type 2 (17β-HSD2) is expressed in human endometrium and its activity has been reported to be linked to cervical cancer. Kitawaki et al., J. Clin. Endocrin. Metab. 2000, 85:3292-3296. 17-beta-Hydroxysteroid dehydrogenase type 3 (17β-HSD3) is expressed in the testes and its modulation may be useful for the treatment of androgen-related disorders.

Androgens and estrogens are active in their 17β-hydroxy configurations, whereas their 17-keto derivatives do not bind to androgen and estrogen receptors and are thus inactive. The conversion between the active and inactive forms (estradiol/estrone and testosterone/androstenedione) of sex hormones is catalyzed by members of the 17β-HSD family. 17β-HSD1 catalyzes the formation of estradiol in breast tissue, which is important for the growth of malignant breast tumors. Labrie et al., Mol. Cell. Endocrinol. 1991, 78:C113-C118. A similar role has been suggested for 17β-HSD4 in colon cancer. English et al., J. Clin. Endocrinol. Metab. 1999, 84:2080-2085. 17β-HSD3 is almost exclusively expressed in the testes and converts androstenedione into testosterone. Deficiency of this enzyme during fetal development leads to male pseudohermaphroditism. Geissler et al., Nat. Genet. 1994, 7:34-39. 17β-HSD3 and various 3α-HSD isozymes are involved in complex metabolic pathways which lead to shuffles between inactive and active forms of androgen. Penning et al., Biochem. J. 2000, 351:67-77. Thus, modulation of certain HSDs can have potentially beneficial effects in the treatment of androgen- and estrogen-related disorders.

The 20-alpha-hydroxysteroid dehydrogenases (20α-HSDs) catalyze the interconversion of progestins (such as between progesterone and 20α-hydroxy progesterone). Other substrates for 20α-HSDs include 17α-hydroxypregnenolone and 17α-hydroxyprogesterone, leading to 20α-OH steroids. Several 20α-HSD isoforms have been identified and 20α-HSDs are expressed in various tissues, including the placenta, ovaries, testes, and adrenals. Peltoketo et al., J. Mol. Endocrinol. 1999, 23:1-11.

The 3-alpha-hydroxysteroid dehydrogenases (3α-HSDs) catalyze the interconversion of the androgens dihydrotestosterone (DHT) and 5α-androstane-3α,17β-diol and the interconversion of the androgens DHEA and androstenedione. Consequently, 3α-HSDs play an important role in androgen metabolism. Ge et al., Biology of Reproduction 1999, 60:855-860.

Despite the previous research done in the field of HSD inhibition, there remains a need for novel compounds that are potent inhibitors of the various families of HSDs and efficacious for the treatment of HSD-mediated conditions such as diabetes, obesity, glaucoma, osteoporosis, cognitive disorders, immune disorders, depression, hypertension, and others.

SUMMARY OF THE INVENTION

In brief, the present invention relates to novel compounds, compositions thereof and methods for modulating the activity of hydroxysteroid dehydrogenases (HSDs), such as 11β-hydroxysteroid dehydrogenases, 17β-hydroxysteroid dehydrogenases, 20α-hydroxysteroid dehydrogenases, and 3α-hydroxysteroid dehydrogenases, including all isoforms thereof, including but not limited to 11β-hydroxysteroid dehydrogenase type 1 (hereinafter "11β-HSD1"), 11β-hydroxysteroid dehydrogenase type 2 (hereinafter "11β-HSD2"), and 17β-hydroxysteroid dehydrogenase type 3 (hereinafter "17β-HSD3"). In one embodiment, the compounds of the invention inhibit HSD activity.

The present invention also relates to methods for treating or preventing diseases or disorders associated with the action of hydroxysteroid dehydrogenases, comprising administering to a patient in need thereof a therapeutically effective amount of a tricyclic compound or a pharmaceutically acceptable salt, solvate, stereoisomer, or prodrug thereof, or a mixture thereof. The invention encompasses both selective and non-selective inhibitors of hydroxysteroid dehydrogenases.

It should be understood that selective and non-selective inhibitors of hydroxysteroid dehydrogenases each have benefits in the treatment or prevention of diseases associated with, for example, abnormal glucose levels or hypothalmic function. The invention also encompasses selective inhibitors of HSDs. Two types of selectivity are contemplated, that with respect to selectivity for HSDs as a class over other types of receptors or gene targets related to glucose metabolism, or that with respect to selectivity for various HSDs or specific isoforms thereof compared to other HSDs or specific isoforms thereof.

In one embodiment, the tricyclic compounds can act as selective or non-selective 11β-HSD inhibitors. The compounds may inhibit the interconversion of inactive 11-keto steroids with their active hydroxy equivalents. The present invention provides methods by which the conversion of the inactive to the active form may be controlled, and is directed to useful therapeutic effects which may be obtained as a result of such control. More specifically, but not exclusively, the invention is concerned with interconversion between cortisone and cortisol in humans.

In another embodiment, the tricyclic compounds of the present invention are orally active.

The tricyclic compounds are also useful for modulation of numerous metabolic functions including, but not limited to, one or more of: (i) regulation of carbohydrate metabolism, (ii) regulation of protein metabolism, (iii) regulation of lipid metabolism, (iv) regulation of normal growth and/or development, (v) influence on cognitive function, and (vi) resistance to stress and mineralocorticoid activity.

The tricyclic compounds may also be useful for inhibiting hepatic gluconeogenesis, and may also be effective to relieve the effects of endogenous glucocorticoids in diabetes mellitus, obesity (including entripetal obesity), neuronal loss and/or the cognitive impairment of old age. Thus, in a further embodiment, the invention provides the use of an inhibitor of HSDs in methods directed to producing one or more therapeutic effects in a patient to whom the tricyclic compound is administered, said therapeutic effects selected from the group consisting of inhibition of hepatic gluconeogenesis, an increase in insulin sensitivity in adipose tissue and muscle, and prevention of or reduction in neuronal loss/cognitive impairment due to glucocorticoid-potentiated neurotoxicity or neural dysfunction or damage.

The invention further provides methods for treating a condition selected from the group consisting of hepatic insulin resistance, adipose tissue insulin resistance, muscle insulin resistance, neuronal loss or dysfunction due to glucocorticoid potentiated neurotoxicity, and any combination of the aforementioned conditions, the methods comprising administering to a patient in need thereof a therapeutically effective amount of a tricyclic compound.

The tricyclic compounds of the invention are compounds having formula (I)

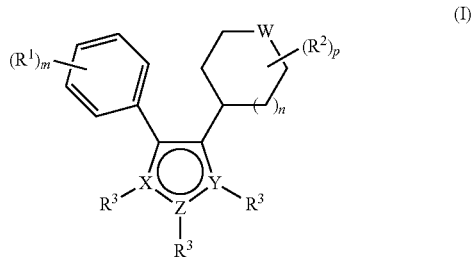

(I)

or pharmaceutically acceptable salts, solvates, stereoisomers, or prodrugs thereof.

In one embodiment, each occurrence of $R^1$ and $R^2$ is independently hydrogen, halogen, nitro, cyano, $(C_1-C_8)$alkyl, $(C_2-C_8)$alkenyl, $(C_2-C_8)$alkynyl, $(C_1-C_8)$haloalkyl, $(C_1-C_8)$hydroxyhaloalkyl, $(C_1-C_8)$alkyl$(C_3-C_7)$cycloalkyl, $(C_1-C_8)$alkyl$(C_3-C_7)$heterocycloalkyl, $(C_1-C_8)$alkylaryl, $(C_1-C_8)$alkylheteroaryl, $(C_3-C_7)$cycloalkyl, $(C_3-C_7)$heterocycloalkyl, aryl, heteroaryl, —OR", —C(O)R', —C(O)OR', —OC(O)R', —OC(O)OR', —C(O)N(R')$_2$, —OC(O)N(R')$_2$, —N(R')$_2$, —NR'C(O)R', —NR'C(O)OR", —NR'C(O)N(R')$_2$, —NR'SO$_2$R", —SR", —S(O)R", —SO$_2$R", —S(O)$_2$OR", —SO$_2$N(R')$_2$, -L-OR", -L-C(O)R', -L-C(O)OR', -L-OC(O)R', -L-OC(O)N(R')$_2$, -L-N(R')$_2$, -L-NR'C(O)OR", -L-C(O)N(R')$_2$, -L-NR'C(O)R", -L-SR", -L-S(O)R", -L-SO$_2$R", -L-SO$_2$N(R')$_2$, or -L-NR'SO$_2$R".

Each occurrence of $R^3$ is independently null, hydrogen, halogen, nitro, cyano, $(C_1-C_8)$alkyl, $(C_2-C_8)$alkenyl, $(C_2-C_8)$alkynyl, $(C_1-C_8)$haloalkyl, $(C_1-C_8)$alkyl$(C_3-C_7)$cycloalkyl, $(C_1-C_8)$alkyl$(C_3-C_7)$heterocycloalkyl, $(C_1-C_8)$alkylaryl, $(C_1-C_8)$alkylheteroaryl, $(C_3-C_7)$cycloalkyl, $(C_3-C_7)$heterocycloalkyl, —OR", —C(O)R', —C(O)OR', —OC(O)R', —OC(O)OR', —C(O)N(R')$_2$, —OC(O)N(R')$_2$, —N(R')$_2$, —NR'C(O)R', —NR'C(O)OR", —NR'C(O)N(R')$_2$, —SR", —S(O)R", —SO$_2$R", —S(O)$_2$OR", —SO$_2$N(R')$_2$, -L-OR", -L-C(O)R', -L-C(O)OR', -L-OC(O)R', -L-OC(O)N(R')$_2$, -L-N(R')$_2$, -L-C(O)N(R')$_2$, -L-NR'C(O)R", -L-SR", -L-S(O)R", -L-SO$_2$R", -L-SO$_2$N(R')$_2$, or -L-NR'SO$_2$R".

W is $C(R)_2$, O, S, NR, NC(O)R', NC(O)OR', NC(O)N(R')$_2$, or NS(O)$_2$R'.

X, Y, and Z are independently C, N, O, or S.

Each occurrence of R is independently hydrogen, halogen, cyano, $(C_1-C_8)$alkyl, $(C_2-C_8)$alkenyl, $(C_2-C_8)$alkynyl, $(C_1-C_8)$haloalkyl, $(C_1-C_8)$hydroxyhaloalkyl, $(C_1-C_8)$alkyl$(C_3-C_7)$cycloalkyl, $(C_1-C_8)$alkyl$(C_3-C_7)$heterocycloalkyl, $(C_1-C_8)$alkylaryl, $(C_1-C_8)$alkylheteroaryl, $(C_3-C_7)$cycloalkyl, $(C_3-C_7)$heterocycloalkyl, aryl, heteroaryl, —OR", —C(O)R', —C(O)OR', —OC(O)R', —OC(O)OR', —C(O)N(R')$_2$, —OC(O)N(R')$_2$, —N(R')$_2$, —NR'C(O)R', —NR'C(O)OR", —NR'C(O)N(R')$_2$, —NR'SO$_2$R", —SR", —S(O)R", —SO$_2$R", —S(O)$_2$OR", —SO$_2$N(R')$_2$, -L-OR", -L-C(O)R', -L-C(O)OR', -L-OC(O)R', -L-OC(O)N(R')$_2$, -L-N(R')$_2$, -L-NR'C(O)OR", -L-C(O)N(R')$_2$, -L-NR'C(O)R", -L-SR", -L-S(O)R", -L-SO$_2$R", -L-SO$_2$N(R')$_2$, or -L-NR'SO$_2$R".

Each occurrence of R' is independently hydrogen, $(C_1-C_8)$alkyl, $(C_2-C_8)$alkenyl, $(C_2-C_8)$alkynyl, $(C_1-C_8)$alkoxy$(C_1-C_8)$alkyl, $(C_1-C_8)$haloalkyl, $(C_1-C_8)$hydroxyalkyl, $(C_1-C_8)$hydroxyhaloalkyl, $(C_1-C_8)$alkyl$(C_3-C_7)$cycloalkyl, $(C_1-C_8)$alkyl$(C_3-C_7)$heterocycloalkyl, $(C_1-C_8)$alkylaryl, $(C_1-C_8)$alkylheteroaryl, $(C_3-C_7)$cycloalkyl, $(C_3-C_7)$heterocycloalkyl, aryl, or heteroaryl.

Alternatively, two R' groups, when attached to the same nitrogen atom, can combine with the nitrogen atom to which they are attached to form a heterocyclic or heteroaryl group.

Each occurrence of R" is independently hydrogen, $(C_1-C_8)$alkyl, $(C_2-C_8)$alkenyl, $(C_2-C_8)$alkynyl, $(C_1-C_8)$alkoxy$(C_1-C_8)$alkyl, $(C_1-C_8)$haloalkyl, $(C_1-C_8)$hydroxyalkyl, $(C_1-C_8)$hydroxyhaloalkyl, $(C_1-C_8)$alkyl$(C_3-C_7)$cycloalkyl, $(C_1-C_8)$alkyl$(C_3-C_7)$heterocycloalkyl, $(C_1-C_8)$alkylaryl, $(C_1-C_8)$alkylheteroaryl, $(C_3-C_7)$cycloalkyl, $(C_3-C_7)$heterocycloalkyl, aryl, or heteroaryl.

Any cycloalkyl portion, heterocycloalkyl portion, aryl portion, or heteroaryl portion is optionally substituted with one to four members selected from the group consisting of hydroxyl, halogen, cyano, nitro, $(C_1-C_8)$alkyl, $(C_2-C_8)$alkenyl, $(C_2-C_8)$alkynyl, $(C_1-C_8)$alkoxy, $(C_1-C_8)$haloalkyl, $(C_1-C_8)$hydroxyalkyl, $(C_1-C_8)$hydroxyhaloalkyl, —OR", —C(O)R', —C(O)

OR', —OC(O)R', —OC(O)OR', —C(O)N(R')$_2$, —OC(O)N(R')$_2$, —N(R')$_2$, —NR'C(O)R', —NR'C(O)OR", —NR'C(O)N(R")$_2$, —NR'SO$_2$R", —SR", —S(O)R", —SO$_2$R", —S(O)$_2$OR", —SO$_2$N(R')$_2$, -L-OR", -L-C(O)R', -L-C(O)OR', -L-OC(O)R', -L-OC(O)N(R')$_2$, -L-N(R')$_2$, -L-NR'C(O)OR", -L-C(O)N(R')$_2$, -L-NR'C(O)R", -L-SR", -L-S(O)R", -L-SO$_2$R", -L-SO$_2$N(R')$_2$, and -L-NR'SO$_2$R".

L is (C$_1$-C$_8$)alkylene.

Variable m is an integer from 1 to 5.

Variable n is an integer from 0 to 2.

Variable p is an integer from 0 to 11.

In another embodiment of compounds of formula (I), at least one occurrence of R' is other than hydrogen.

It should be understood that, notwithstanding the provisions of formula (I):

no occurrence of R' is —SO$_2$NH$_2$, —SO$_2$NH-alkyl, or —SO$_2$-alkyl;

no occurrence of R$^2$ is —C(O)N(R')$_2$, hydroxyalkyl, alkoxyalkyl, or —CO$_2$H; and no occurrence of R$^3$ is hydroxyl, hydroxyalkyl, alkoxyalkyl, —NH$_2$, —NH-alkyl, aminoalkyl, —C(O)O-alkyl, —C(O)-alkyl, or -L—OC(O)-alkyl.

Furthermore, when X is S and Y is N, then no occurrence of R' is:

cyano or nitro;

—OR", —SR", hydroxyalkyl, or —OC(O)-alkyl;

—NH$_2$, —NHR', —N(alkyl)$_2$, —NR'C(O)R', —NR'C(O)OR", or —NR'C(O)N(R')$_2$; or —C(O)-alkyl, —C(O)-aryl, —CO$_2$H, —C(O)O-alkyl, —C(O)N(R')$_2$, or -L-C(O)R'.

In addition, the following compounds are excluded from the scope of the present invention:

4-cyclohexyl-5-(3-fluorophenyl)-2-methyloxazole

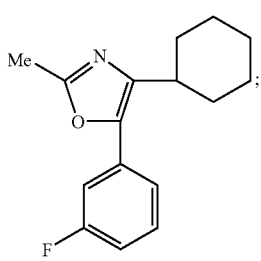 [SMILES: Cc1nc(C2CCCCC2)c(-c2cccc(F)c2)o1]

4-cyclohexyl-2-ethyl-5-(3-fluorophenyl)oxazole

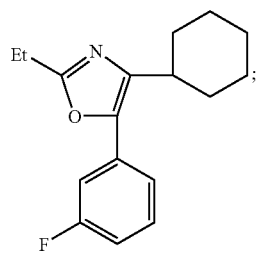 [SMILES: CCc1nc(C2CCCCC2)c(-c2cccc(F)c2)o1]

5-(4-chlorophenyl)-4-cyclopentyl-2-[(1S)-1-fluoroethyl]thiazole

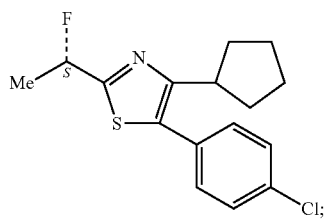

5-(4-chlorophenyl)-4-cyclohexyl-2-ethylthiazole

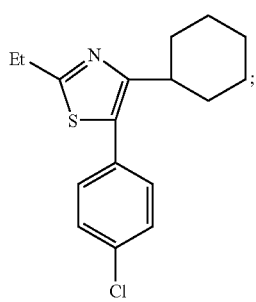

4-cyclopentyl-2-ethyl-5-(4-ethylphenyl)thiazole

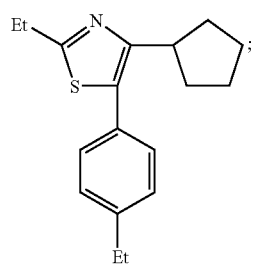 [SMILES: CCc1ccc(-c2sc(CC)nc2C2CCCC2)cc1]

5-(3-chlorophenyl)-4-cyclopentyl-2-ethylthiazole

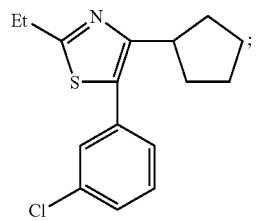 [SMILES: CCc1nc(C2CCCC2)c(-c2cccc(Cl)c2)s1]

4-cyclopentyl-2-ethyl-5-(3-methylphenyl)thiazole

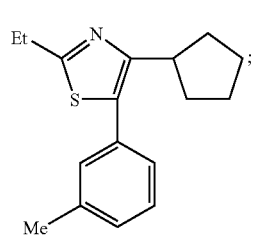

5-(2-chlorophenyl)-4-cyclopentyl-2-ethylthiazole

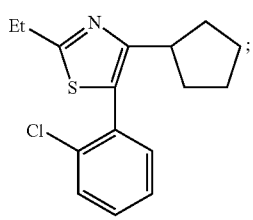 [SMILES: CCc1nc(C2CCCC2)c(-c2ccccc2Cl)s1]

4-cyclopentyl-2-ethyl-5-(2-methylphenyl)thiazole

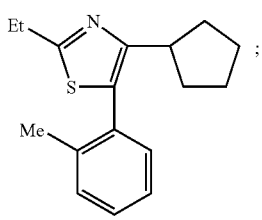 [SMILES: CCc1nc(C2CCCC2)c(-c2ccccc2C)s1]

4-cyclohexyl-5-(3-fluorophenyl)-2-methyloxazole

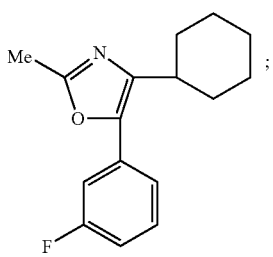 [SMILES: Cc1nc(C2CCCCC2)c(-c2cccc(F)c2)o1]

3-[4-(4-fluorophenyl)-2-methyl-5-thiazolyl]-1-pyrrolidin-ecarboxylic acid, ethyl ester

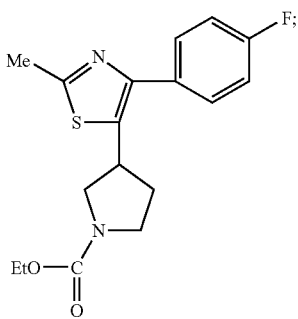 [SMILES: CCOC(=O)N1CCC(c2sc(C)nc2-c2ccc(F)cc2)C1]

4-(4-fluorophenyl)-2-methyl-5-(3-pyrrolidinyl)thiazole

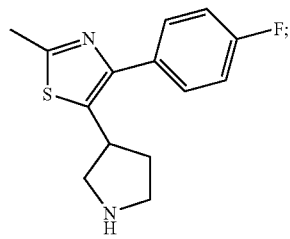 [SMILES: Cc1nc(-c2ccc(F)cc2)c(C2CCNC2)s1]

1-(4-fluorophenyl)-4-[3-[4-(4-fluorophenyl)-2-methyl-5-thiazolyl]-1-pyrrolidinyl]-1-butanone

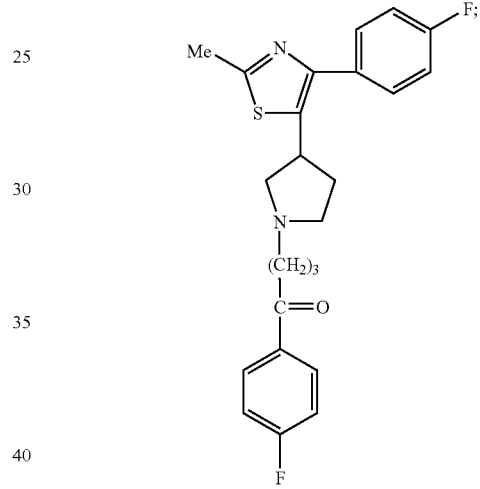

4-(4-fluorophenyl)-5-[1-[3-[2-(4-fluorophenyl)-1,3-dioxolan-2-yl]propyl]-3-pyrrolidinyl]-2-methylthiazole

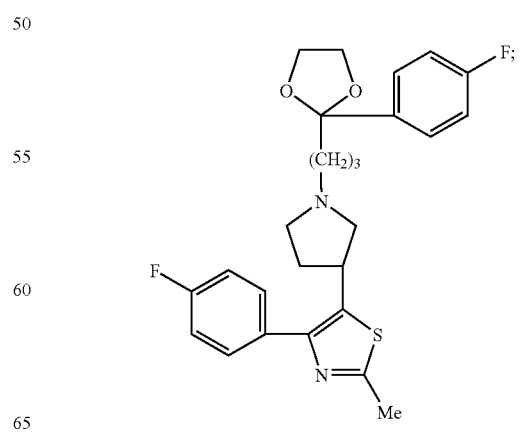

4-cyclohexyl-5-(3-fluorophenyl)-2-methyloxazole

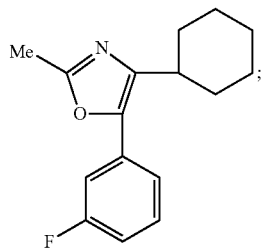 [SMILES: Cc1nc(C2CCCCC2)c(-c2cccc(F)c2)o1]

4-[5-cyclohexyl-2-(methylthio)-4-thiazolyl]-2,6-bis(1,1-dimethylethyl)phenol

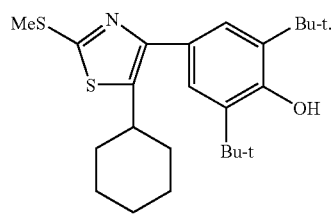

In one embodiment, the invention provides pharmaceutical compositions comprising a tricyclic compound and a pharmaceutically acceptable vehicle, carrier, excipient, or diluent.

In another embodiment, the invention provides pharmaceutical compositions comprising a tricyclic compound and one or more additional therapeutic agents.

In a further embodiment, the invention provides a method for treating a condition or disorder selected from the group consisting of diabetes, syndrome X, obesity, polycystic ovarian disease, an eating disorder, craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia, Cushing's syndrome, hypertension, atherosclerosis, vascular restenosis, retinopathy, nephropathy, neurodegenerative disease, neuropathy, muscle wasting, a cognitive disorder, dementia, depression, psoriasis, glaucoma, osteoporosis, a viral infection, an inflammatory disorder, and an immune disorder, comprising administering to a patient in need thereof a therapeutically effective amount of a tricyclic compound of formula (I).

In yet another embodiment, the invention provides a method for treating a hydroxysteroid dehydrogenase-mediated condition or disorder, comprising administering to a patient in need thereof a therapeutically effective amount of a compound of formula (I).

In a further embodiment, the invention provides a method for modulating a hydroxysteroid dehydrogenase, comprising administering to a patient in need thereof a therapeutically effective amount of a tricyclic compound of formula (I).

In still another embodiment, the invention provides a method for modulating the function of a hydroxysteroid dehydrogenase in a cell, comprising contacting the cell with a tricyclic compound of formula (I).

In one embodiment, the invention provides a method for treating an 11β-HSD1-mediated condition or disorder, comprising administering to a patient in need thereof a therapeutically effective amount of a tricyclic compound of formula (I).

In another embodiment, the invention provides a method for modulating the function of 11β-HSD1 in a cell, comprising administering to a patient in need thereof a therapeutically effective amount of a tricyclic compound of formula (I).

In a further embodiment, the invention provides a method for modulating 11β-HSD1, comprising administering to a patient in need thereof a therapeutically effective amount of a tricyclic compound of formula (I).

These and other embodiments of the present invention will be evident upon reference to the following detailed description. To that end, certain patent and other documents are cited herein to more specifically set forth various embodiments of the present invention. Each of these documents is hereby incorporated by reference in its entirety.

DETAILED DESCRIPTION

As used herein, the terms have the following meanings:

The term "alkyl" as used herein refers to a straight or branched chain saturated hydrocarbon having the indicated number of carbon atoms. For example, $(C_1-C_6)$alkyl is meant to include, but is not limited to, methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein below.

The term "alkenyl" as used herein refers to a straight or branched chain unsaturated hydrocarbon having the indicated number of carbon atoms and at least one double bond. Examples of a $(C_2-C_s)$alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" as used herein refers to a straight or branched chain unsaturated hydrocarbon having the indicated number of carbon atoms and at least one triple bond. Examples of a $(C_2-C_8)$alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkylene" refers to a divalent straight or branched alkyl group (e.g., an alkyl group attached to two other moieties, oftentimes as a linking group). Examples of a $(C_1-C_7)$alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. An alkylene group can be unsubstituted or optionally substituted with one or more substituents as described herein below. For instance, examples of a $(C_3)$ alkylene-OH include —$CH_2CH_2CH_2$—OH, —$CH_2CH(OH)CH_3$, —$C(CH_3)_2OH$, —$CH(OH)CH_2CH_3$, and —$CH(CH_3)CH_2$—OH.

The term "alkoxy" as used herein refers to a straight or branched —O-alkyl group having the indicated number of carbon atoms. For example, a $(C_1-C_6)$alkoxy group includes, but is not limited to, —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl" as used herein refers to a straight or branched alkyl group (typically one to six carbon atoms) wherein one or more of the alkyl group's hydrogen atoms is replaced with an amine of formula —N(R$^a$)$_2$, wherein each occurrence of R$^a$ is independently —H or (C$_1$-C$_6$)alkyl. Examples of aminoalkyl groups include, but are not limited to, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$CH$_2$CH$_2$CH$_2$NH$_2$, —CH$_2$CH$_2$CH$_2$CH$_2$CH$_2$CH$_2$NH$_2$, —CH$_2$CH$_2$CH$_2$N(CH$_3$)$_2$, t-butylaminomethyl, isopropylaminomethyl, and the like.

The term "aryl" as used herein refers to a 6- to 14-membered monocyclic, bicyclic, or tricyclic aromatic hydrocarbon ring system. Examples of an aryl group include, but are not limited to, phenyl and naphthyl. An aryl group can be unsubstituted or optionally substituted with one or more substituents as described herein below.

The term "cycloalkyl" as used herein refers to a 3- to 14-membered saturated or unsaturated non-aromatic monocyclic, bicyclic, or tricyclic hydrocarbon ring system. The bicyclic or tricyclic hydrocarbon ring systems may be spiro-fused. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, spiro[5,4]decane, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene. A cycloalkyl group can be unsubstituted or optionally substituted with one or more substituents as described herein below.

The terms "halo", "halogen", "halide" and the like as used herein refer to —F, —Cl, —Br, or —I.

The term "haloalkyl," as used herein, refers to a straight or branched alkyl group wherein one or more of the alkyl group's hydrogen atoms is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroaryl" as used herein refers to an aromatic heterocycle ring of 5 to 14 members, having at least one heteroatom selected from nitrogen, oxygen and sulfur, and containing at least 1 carbon atom. Heteroaryls may be monocyclic, bicyclic, or tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl. A heteroaryl group can be unsubstituted or optionally substituted with one or more substituents as described herein below.

As used herein, the term "heteroatom" is meant to include oxygen (O), nitrogen (N), and sulfur (S).

The term "heterocycle" or "heterocycloalkyl" as used herein refers to 5- to 14-membered ring systems which are either saturated, unsaturated, or aromatic, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized. Heterocycles may be monocyclic, bicyclic, or tricyclic ring systems. The bicyclic or tricyclic ring systems may be spiro-fused. The bicyclic and tricyclic ring systems may encompass a heterocycle or heteroaryl fused to a benzene ring. The heterocycle may be attached via any heteroatom or carbon atom. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "hydroxyalkyl" as used herein refers to a straight or branched alkyl group having the indicated number of carbon atoms, wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "hydroxyhaloalkyl" as used herein refers to a straight or branched alkyl group having the indicated number of carbon atoms, wherein one or more of the alkyl group's hydrogen atoms is replaced with a halogen atom, which can be the same or different, and in addition one or more of the alkyl group's hydrogen atoms is replaced with an —OH group. Non-limiting examples of hydroxyhaloalkyl groups include —C(CH$_3$)(CF$_3$)OH and —C(CF$_3$)$_2$OH.

Substituents for the groups referred to as alkyl, heteroalkyl, alkylene, alkenyl, alkynyl, cycloalkyl, heterocycloalkyl, cycloalkenyl, and heterocycloalkenyl can be a variety of groups including, but not limited to, —OR$^a$, =O, =NR$^a$, =N—OR$^a$, —NR$^a$R$^b$, —SR$^a$, -halo, —SiR$^a$R$^b$R$^c$, —OC(O)R$^a$, —C(O)R$^a$, —CO$_2$R$^a$, —CONR$^a$R$^b$, —OC(O)NR$^a$R$^b$, —NR$^b$C(O)R$^a$, —NR$^c$C(O)NR$^a$R$^b$, NR$^a$SO$_2$NR$^a$R$^b$, —NR$^b$CO$_2$R$^a$, —NHC(NH$_2$)=NH, —NR$^a$C(NH$_2$)=NH, —NHC(NH$_2$)=NR$^a$, —S(O)R$^a$, —SO$_2$R$^a$, —SO$_2$NR$^a$R$^b$, —NR$^b$SO$_2$R$^a$, —CN and —NO$_2$, in a number ranging from zero to three, with those groups having zero, one or two substituents being exemplary. R$^a$, R$^b$ and R$^c$ independently may refer to, e.g., hydrogen, unsubstituted (C$_1$-C$_8$)alkyl, unsubstituted hetero(C$_1$-C$_8$)alkyl, unsubstituted aryl, and aryl substituted with one to three substituents selected from, e.g., -halo, unsubstituted alkyl, unsubstituted alkoxy, unsubstituted thioalkoxy, and unsubstituted aryl(C$_1$-C$_4$)alkyl. When R$^a$ and R$^b$ are attached to the same nitrogen atom, they can be combined with the nitrogen atom to form, e.g., a 5-, 6- or 7-membered ring. For example, —NR$^a$R$^b$ is meant to include 1-pyrrolidinyl and 4-morpholinyl. An alkyl or heteroalkyl group will have from zero to three substituents, with those groups having two or fewer substituents being exemplary in the present invention. In some embodiments, an alkyl or heteroalkyl radical will be unsubstituted or monosubstituted. An alkyl or heteroalkyl radical can be unsubstituted.

From the above discussion of substituents, one of skill in the art will understand that the term "alkyl" is meant to include groups such as trihaloalkyl (e.g., —CF$_3$ and —CH$_2$CF$_3$).

Representative examples of substituents for alkyl and heteroalkyl radicals are —OR$^a$, =O, —NR$^a$R$^b$, —SR$^a$, -halo, —SiR$^a$R$^b$R$^c$, —OC(O)R$^a$, —C(O)R$^a$, —CO$_2$R$^a$, —C(O)NR$^a$R$^b$, —OC(O)NR$^a$R$^b$, —NR$^b$C(O)R$^a$, —NR$^b$CO$_2$R$^a$, —NR$^c$SO$_2$NR$^a$R$^b$, —S(O)R$^a$, —SO$_2$R$^a$, —SO$_2$NR$^a$R$^b$, —NR$^b$SO$_2$R$^a$, —CN and —NO$_2$, where R$^a$, R$^b$ and R$^c$ are as defined above. Exemplary substituents are selected from: —OR$^a$, =O, —NR$^a$R$^b$, -halo, —OC(O)R$^a$, —CO$_2$R$^a$, —C(O)NR$^a$R$^b$, —OC(O)NR$^a$R$^b$, —NR$^b$C(O)R$^a$, —NR$^b$CO$_2$R$^a$, —NR$^c$SO$_2$NR$^a$R$^b$, —SO$_2$R$^a$, —SO$_2$NR$^a$R$^b$, —NR$^b$SO$_2$R$^a$, —CN and —NO$_2$.

Similarly, representative examples of substituents for aryl and heteroaryl groups are -halo, —OR$^a$, —OC(O)R$^a$, —NR$^a$R$^b$, —SR$^a$, —R$^a$, —CN, —NO$_2$, —CO$_2$R$^a$, —C(O)NR$^a$R$^b$, —C(O)R$^a$, —OC(O)NR$^a$R$^b$, —NR$^b$C(O)R$^a$, —NR$^b$CO$_2$R$^b$, —NR$^c$C(O)NR$^a$R$^b$, —NR$^c$SO$_2$NR$^a$R$^b$, —NHC(NH$_2$)=NH, —NR$^a$C(NH$_2$)=NH, —NH—C(NH$_2$)=NR$^a$, —S(O)R$^a$, —SO$_2$R$^a$, —SO$_2$NR$^a$R$^b$, —NR$^b$SO$_2$R$^a$, —N$_3$, —CH(Ph)$_2$, perfluoroalkoxy and perfluoro(C$_1$-C$_4$) alkyl, in a number ranging from zero to the total number of open valences on the aromatic ring system. R$^a$, R$^b$ and R$^c$ independently may be, e.g., hydrogen, unsubstituted (C$_1$-C$_8$) alkyl, unsubstituted hetero(C$_1$-C$_8$)alkyl, unsubstituted aryl, unsubstituted heteroaryl, unsubstituted aryl(C$_1$-C$_4$)alkyl, and unsubstituted aryloxy(C$_1$-C$_4$)alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer from 0 to 2. Alternatively, two of the substituents on adjacent atoms of an aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer from 1 to 3. One of the single bonds of the new ring so formed may optionally be replaced with a double bond. Alternatively, two of the substituents on adjacent atoms of an aryl or heteroaryl ring may optionally be replaced with a substituent of the formula —(CH$_2$)$_s$—X—(CH$_2$)$_t$—, where s and t independently are integers from 0 to 3, and X is —O—, —NR$^a$—, —S—, —S(O)—, —S(O)$_2$—, or —S(O)$_2$NR$^a$—. The substituent R$^a$ in —NR$^a$— and —S(O)$_2$NR$^a$— may be, e.g., hydrogen or unsubstituted (C$_1$-C$_6$)alkyl.

It is to be understood that the substituent —CO$_2$H, as used herein, may be optionally replaced with bioisosteric replacements such as:

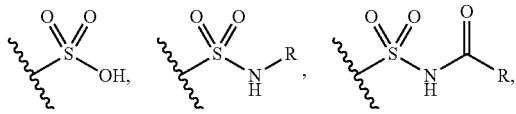

-continued

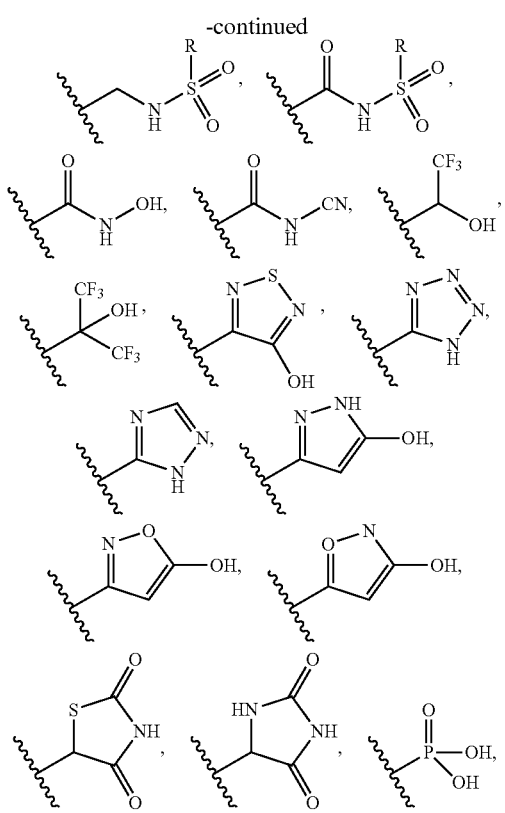

and the like. See, e.g., *The Practice of Medicinal Chemistry*; Wermuth, C. G., Ed.; Academic Press: New York, 1996; p. 203.

The tricyclic compounds of the present invention can also exist in various isomeric forms, including stereochemical, configurational, geometric and conformational isomers, as well as exist in various tautomeric forms, particularly those that differ in the point of attachment of a hydrogen atom. As used herein, the term "isomer" is intended to encompass all isomeric forms of a tricyclic compound, including tautomeric forms of the compound.

Certain tricyclic compounds may have asymmetric centers and therefore exist in different enantiomeric or diastereomeric forms. A tricyclic compound can be in the form of an optical isomer or a diastereomer. Accordingly, the invention encompasses tricyclic compounds and their uses as described herein in the form of their optical isomers, diastereomers and mixtures thereof, including a racemic mixture. Optical isomers of the tricyclic compounds can be obtained by known techniques such as asymmetric synthesis, chiral chromatography, simulated moving bed technology, or via chemical separation of stereoisomers through the employment of optically active resolving agents.

As used herein and unless otherwise indicated, the term "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, or greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

A tricyclic compound can be in the form of a pharmaceutically acceptable salt. Depending on the its structure, the phrase "pharmaceutically acceptable salt" as used herein refers to a pharmaceutically acceptable organic or inorganic acid or base salt of a tricyclic compound. Representative pharmaceutically acceptable salts include, e.g., alkali metal salts, alkali earth salts, ammonium salts, water-soluble, and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. Furthermore, a pharmaceutically acceptable salt can have more than one charged atom in its structure. In this instance the pharmaceutically acceptable salt can have multiple counterions. Hence, a pharmaceutically acceptable salt can have one or more charged atoms and/or one or more counterions.

As used herein, the term "isolated and purified form" means that when isolated (e.g., from other components of a synthetic organic chemical reaction mixture), the isolate contains at least 30%, at least 35%, at least 40%, at least 45%, at least 50%, at least 55%, at least 60%, at least 65%, at least 70%, at least 75%, at least 80%, at least 85%, at least 90%, at least 95%, or at least 98% of a tricyclic compound by weight of the isolate. In one embodiment, the isolate contains at least 95% of a tricyclic compound by weight of the isolate.

As used herein, the term "prodrug" means a derivative of a compound that can hydrolyze, oxidize, or otherwise react under biological conditions (in vitro or in vivo) to provide an active compound, particularly a tricyclic compound. Examples of prodrugs include, but are not limited to, derivatives and metabolites of a tricyclic compound that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). For instance, prodrugs of compounds with carboxyl functional groups may be the lower alkyl esters of the carboxylic acids. The carboxylate esters are conveniently formed by esterifying any of the carboxylic acid moieties present on the molecule. Prodrugs can typically be prepared using well known methods, such as those described by *Burger's Medicinal Chemistry and Drug Discovery*, 6$^{th}$ ed. (Donald J. Abraham ed., 2001, Wiley), and *Design and Application of Prodrugs* (H. Bundgaard ed., 1985, Harwood Academic Publishers Gmfh).

As used herein, the terms "treat", "treating" and "treatment" refer to eradication or amelioration of a disease or symptoms associated with a disease. In certain embodiments, such terms refer to minimizing the spread or worsening of the disease resulting from the administration of one or more prophylactic or therapeutic agents to a patient with such a disease.

As used herein, the terms "prevent", "preventing" and "prevention" refer to prevention of the onset, recurrence or spread of a disease in a patient resulting from the administration of a prophylactic or therapeutic agent.

The term "effective amount" as used herein refers to an amount of a tricyclic compound or other active ingredient sufficient to provide a therapeutic or prophylactic benefit in the treatment or prevention of a disease or to delay or minimize symptoms associated with a disease. Further, a therapeutically effective amount with respect to a tricyclic compound means that amount of therapeutic agent alone, or in combination with other therapies, that provides a therapeutic benefit in the treatment or prevention of a disease. Used in connection with a tricyclic compound, the term can encompass an amount that improves overall therapy, reduces or avoids symptoms or causes of disease, or enhances the therapeutic efficacy of or synergies with another therapeutic agent.

The terms "modulate", "modulation" and the like refer to the ability of a compound to increase or decrease the function, or activity, of a target (e.g., 11β-HSD1). The term "modulation", as used herein in its various forms, is intended to encompass inhibition, antagonism, partial antagonism, activation, agonism and/or partial agonism of the function, or activity, of a target (e.g., 11β-HSD1). 11β-HSD1 inhibitors are compounds that, e.g., bind to, partially or totally block stimulation, decrease, prevent, delay activation, inactivate, desensitize, or down regulate signal transduction. 11β-HSD1 activators are compounds that, e.g., bind to, stimulate, increase, open, activate, facilitate, enhance activation, sensitize or up regulate signal transduction.

The ability of a compound to modulate a target (e.g., 11β-HSD1) can be demonstrated, e.g., in an enzymatic assay or a cell-based assay. For example, the inhibition of 11β-HSD1 may decrease cortisol levels in a patient and/or increase cortisone levels in a patient by blocking the conversion of cortisone to cortisol. Alternatively, the inhibition of 11β-HSD2 can increase cortisol levels in a patient and/or decrease cortisone levels in a patient by blocking the conversion of cortisol to cortisone.

A "patient" includes an animal (e.g., cow, horse, sheep, pig, chicken, turkey, quail, cat, dog, mouse, rat, rabbit or guinea pig). In one embodiment, a "patient" includes a mammal such as a non-primate and a primate (e.g., monkey and human). In another embodiment, a patient is a human. In specific embodiments, the patient is a human infant, child, adolescent or adult.

The term "HSD" as used herein refers to hydroxysteroid dehydrogenase enzymes in general, including, but not limited to, 11-beta-hydroxysteroid dehydrogenases (11β-HSDs), 17-beta-hydroxysteroid dehydrogenases (17β-HSDs), 20-alpha-hydroxysteroid dehydrogenases (20α-HSDs), 3-alpha-hydroxysteroid dehydrogenases (3α-HSDs), and all isoforms thereof.

The term "11β-HSD1" as used herein refers to the 11-beta-hydroxysteroid dehydrogenase type 1 enzyme, variant, or isoform thereof. 11β-HSD1 variants include proteins substantially homologous to native 11β-HSD1, i.e., proteins having one or more naturally or non-naturally occurring amino acid deletions, insertions or substitutions (e.g., 11β-HSD1 derivatives, homologs and fragments). The amino acid sequence of a 11β-HSD1 variant is, e.g., at least about 80% identical to a native 11β-HSD1, or at least about 90% identical, or at least about 95% identical.

The term "11β-HSD2" as used herein refers to the 11-beta-hydroxysteroid dehydrogenase type 2 enzyme, variant, or isoform thereof 11β-HSD2 variants include proteins substantially homologous to native 11β-HSD2, i.e., proteins having one or more naturally or non-naturally occurring amino acid deletions, insertions or substitutions (e.g., 11β-HSD2 derivatives, homologs and fragments). The amino acid sequence of a 11β-HSD2 variant is, e.g., at least about 80% identical to a native 11β-HSD2, or at least about 90% identical, or at least about 95% identical. See Bart et al., J. Med. Chem. 2002, 45:3813-3815.

The term "17β-HSD3" as used herein refers to the 17-beta-hydroxysteroid dehydrogenase type 3 enzyme, variant, or isoform thereof 17β-HSD3 variants include proteins substantially homologous to native 17β-HSD3, i.e., proteins having one or more naturally or non-naturally occurring amino acid deletions, insertions or substitutions (e.g., 17β-HSD3 derivatives, homologs and fragments). The amino acid sequence of a 17β-HSD3 variant is, e.g., at least about 80% identical to a native 17β-HSD3, or at least about 90% identical, or at least about 95% identical.

As used herein, the term "HSD-responsive condition or disorder" and related terms and phrases refer to a condition or disorder that responds favorably to modulation of a hydroxysteroid dehydrogenase enzyme (HSD). Favorable responses to HSD modulation include alleviation or abrogation of the disease and/or its attendant symptoms, inhibition of the disease (i.e., arrest or reduction of the development of the disease, or its clinical symptoms), and regression of the disease or its clinical symptoms. An HSD-responsive condition or disease may be completely or partially responsive to HSD modulation. An HSD-responsive condition or disorder may be associated with inappropriate, e.g., less than or greater than normal, HSD activity and is at least partially responsive to or affected by HSD modulation (e.g., an HSD inhibitor results in some improvement in patient well-being in at least some patients). Inappropriate HSD functional activity might arise as the result of HSD expression in cells which normally do not express HSD, decreased HSD expression or increased HSD expression. An HSD-responsive condition or disorder may include condition or disorder mediated by any HSD or isoform thereof.

As used herein, the term "11β-HSD1-responsive condition or disorder" and related terms and phrases refer to a condition or disorder that responds favorably to modulation of 11β-HSD1 activity. Favorable responses to 11β-HSD1 modulation include alleviation or abrogation of the disease and/or its attendant symptoms, inhibition of the disease (i.e., arrest or reduction of the development of the disease, or its clinical symptoms), and regression of the disease or its clinical symptoms. An 11β-HSD1-responsive condition or disease may be completely or partially responsive to 11β-HSD1 modulation. An 11β-HSD1-responsive condition or disorder may be associated with inappropriate, e.g., less than or greater than normal, 11β-HSD1 activity and is at least partially responsive to or affected by 11β-HSD1 modulation (e.g., a 11β-HSD1 inhibitor results in some improvement in patient well-being in at least some patients). Inappropriate 11β-HSD1 functional activity might arise as the result of 11β-HSD1 expression in cells which normally do not express 11β-HSD1, decreased 11β-HSD1 expression or increased 11β-HSD1 expression. A 11β-HSD1-responsive condition or disorder may include a 11β-HSD1-mediated condition or disorder.

As used herein, the term "11β-HSD2-responsive condition or disorder" and related terms and phrases refer to a condition or disorder that responds favorably to modulation of 11β-HSD2 activity. Favorable responses to 11β-HSD2 modulation include alleviation or abrogation of the disease and/or its attendant symptoms, inhibition of the disease (i.e., arrest or reduction of the development of the disease, or its clinical symptoms), and regression of the disease or its clinical symptoms. An 11β-HSD2-responsive condition or disease may be completely or partially responsive to 11β-HSD2 modulation. An 11β-HSD2-responsive condition or disorder may be associated with inappropriate, e.g., less than or greater than normal, 11β-HSD2 activity and is at least partially responsive to or affected by 11β-HSD2 modulation (e.g., a 11β-HSD2 inhibitor results in some improvement in patient well-being in at least some patients). Inappropriate 11β-HSD2 functional activity might arise as the result of 11β-HSD2 expression in cells which normally do not express 11β-HSD2, decreased 11β-HSD2 expression or increased 11β-HSD2 expression. A 11β-HSD2-responsive condition or disorder may include a 11β-HSD2-mediated condition or disorder.

As used herein, the term "17β-HSD3-responsive condition or disorder" and related terms and phrases refer to a condition or disorder that responds favorably to modulation of 17β-HSD3 activity. Favorable responses to 17β-HSD3 modulation include alleviation or abrogation of the disease and/or its attendant symptoms, inhibition of the disease (i.e., arrest or reduction of the development of the disease, or its clinical symptoms), and regression of the disease or its clinical symptoms. An 17β-HSD3-responsive condition or disease may be completely or partially responsive to 17β-HSD3 modulation. An 17β-HSD3-responsive condition or disorder may be associated with inappropriate, e.g., less than or greater than normal, 17β-HSD3 activity and is at least partially responsive to or affected by 17β-HSD3 modulation (e.g., a 17β-HSD3 inhibitor results in some improvement in patient well-being in at least some patients). Inappropriate 17β-HSD3 functional activity might arise as the result of 17β-HSD3 expression in cells which normally do not express 17β-HSD3, decreased 17β-HSD3 expression or increased 17β-HSD3 expression. A 17β-HSD3-responsive condition or disorder may include a 17β-HSD3-mediated condition or disorder.

As used herein, the term "HSD-mediated condition or disorder" and related terms and phrases refer to a condition or disorder characterized by inappropriate, e.g., less than or greater than normal, activity of a hydroxysteroid dehydrogenase (HSD). An HSD-mediated condition or disorder may be completely or partially characterized by inappropriate HSD activity. However, an HSD-mediated condition or disorder is one in which modulation of an HSD results in some effect on the underlying condition or disease (e.g., an HSD inhibitor results in some improvement in patient well-being in at least some patients).

As used herein, the term "11β-HSD1-mediated condition or disorder" and related terms and phrases refer to a condition or disorder characterized by inappropriate, e.g., less than or greater than normal, 11β-HSD1 activity. A 11β-HSD1-mediated condition or disorder may be completely or partially characterized by inappropriate 11β-HSD1 activity. However, a 11β-HSD1-mediated condition or disorder is one in which modulation of 110-HSD1 results in some effect on the underlying condition or disease (e.g., a 11β-HSD1 inhibitor results in some improvement in patient well-being in at least some patients).

As used herein, the term "11β-HSD2-mediated condition or disorder" and related terms and phrases refer to a condition or disorder characterized by inappropriate, e.g., less than or greater than normal, 11β-HSD2 activity. A 11β-HSD2-mediated condition or disorder may be completely or partially characterized by inappropriate 11β-HSD2 activity. However, a 11β-HSD2-mediated condition or disorder is one in which modulation of 11β-HSD2 results in some effect on the underlying condition or disease (e.g., a 11β-HSD2 inhibitor results in some improvement in patient well-being in at least some patients).

As used herein, the term "17β-HSD3-mediated condition or disorder" and related terms and phrases refer to a condition or disorder characterized by inappropriate, e.g., less than or greater than normal, 17β-HSD3 activity. A 17β-HSD3-mediated condition or disorder may be completely or partially characterized by inappropriate 17β-HSD3 activity. However, a 17β-HSD3-mediated condition or disorder is one in which modulation of 1713-HSD3 results in some effect on the underlying condition or disease (e.g., a 17β-HSD3 inhibitor results in some improvement in patient well-being in at least some patients).

As used herein, "syndrome X" refers to a collection of abnormalities including hyperinsulinemia; obesity; elevated levels of triglycerides, uric acid, fibrinogen, small dense LDL particles and plasminogen activator inhibitor 1 (PAI-1); and decreased levels of HDL cholesterol. Syndrome X is further meant to include metabolic syndrome.

The following abbreviations are used herein and have the indicated definitions:

DCM is dichloromethane; DIPEA is diisopropylethylamine; DMAP is 4-dimethylaminopyridine; DMEM is Dulbecco's Modified Eagle Medium; EtOAc is ethyl acetate; HPLC is high-performance liquid chromatography; LAH is lithium aluminum hydride; MeOH is methanol; MS is mass spectrometry; NMR is nuclear magnetic resonance; PBS is phosphate-buffered saline; RT is room temperature; SPA is scintillation proximity assay; TBAF is tetrabutylammonium fluoride; TBS is tert-butyldimethylsilyl; THF is tetrahydrofuran; TLC is thin-layer chromatography; prep TLC is preparative thin-layer chromatography; and TMS is trimethylsilyl.

It is understood that the word "tricyclic" in the term "tricyclic compound", when used in reference to compounds of the invention, refers to the tricyclic core of compounds of formula (I). Therefore, the term "tricyclic compound", when used in reference to compounds of the invention, may encompass compounds of formula (I) that have one or more cyclic moieties in addition of the tricyclic core.

Compounds of the Invention

The present invention provides compounds of formula (I) as well as pharmaceutically acceptable salts, solvates, stereoisomers or prodrugs thereof, or mixtures thereof, collectively referred to as "the tricyclic compounds" as appropriate:

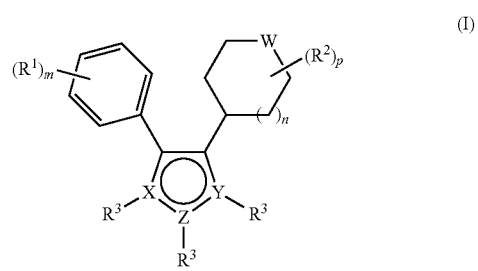

(I)

wherein $R^1$, $R^2$, $R^3$, W, X, Y, Z, m, n, and p are defined below.

In some embodiments, optionally in combination with other embodiments herein described, each occurrence of $R^1$ and $R^2$ is independently hydrogen, halogen, nitro, cyano, $(C_1-C_8)$alkyl, $(C_2-C_8)$alkenyl, $(C_2-C_8)$alkynyl, $(C_1-C_8)$haloalkyl, $(C_1-C_8)$hydroxyhaloalkyl, $(C_1-C_8)$alkyl$(C_3-C_7)$cycloalkyl, $(C_1-C_8)$alkyl$(C_3-C_7)$heterocycloalkyl, $(C_1-C_8)$alkylaryl, $(C_1-C_8)$alkylheteroaryl, $(C_3-C_7)$cycloalkyl, $(C_3-C_7)$heterocycloalkyl, aryl, heteroaryl, —OR", —C(O)R', —C(O)OR', —OC(O)R', —OC(O)OR', —C(O)N(R')$_2$, —OC(O)N(R')$_2$, —N(R')$_2$, —NR'C(O)R', —NR'C(O)OR", —NR'C(O)N(R')$_2$, —NR'SO$_2$R", —SR", —S(O)R", —SO$_2$R", —S(O)$_2$OR", —SO$_2$N(R')$_2$, -L-OR", -L-C(O)R', -L-C(O)OR', -L-OC(O)R', -L-OC(O)N(R')$_2$, -L-N(R')$_2$, -L-NR'C(O)OR", -L-C(O)N(R')$_2$, -L-NR'C(O)R", -L-SR", -L-S(O)R", -L-SO$_2$R", -L-SO$_2$N(R')$_2$, or -L-NR'SO$_2$R".

Each occurrence of $R^3$ is independently null, hydrogen, halogen, nitro, cyano, $(C_1-C_8)$alkyl, $(C_2-C_8)$alkenyl, $(C_2-C_8)$alkynyl, $(C_1-C_8)$haloalkyl, $(C_1-C_8)$alkyl$(C_3-C_7)$cycloalkyl, $(C_1-C_8)$alkyl$(C_3-C_7)$heterocycloalkyl, $(C_1-C_8)$alkylaryl, $(C_1-C_8)$alkylheteroaryl, $(C_3-C_7)$cycloalkyl, $(C_3-C_7)$heterocycloalkyl, —OR", —C(O)R', —C(O)OR', —OC(O)R', —OC(O)OR', —C(O)N(R')$_2$, —OC(O)N(R')$_2$, —N(R')$_2$, —NR'C(O)R', —NR'C(O)OR", —NR'C(O)N(R')$_2$, —SR", —S(O)R", —SO$_2$R", —S(O)$_2$OR", —SO$_2$N(R')$_2$, -L-OR", -L-C(O)R', -L-C(O)OR', -L-OC(O)R', -L-OC(O)N(R')$_2$, -L-N(R')$_2$, -L-C(O)N(R')$_2$, -L-NR'C(O)R", -L-SR", -L-S(O)R", -L-SO$_2$R", -L-SO$_2$N(R')$_2$, or -L-NR'SO$_2$R".

W is $C(R)_2$, O, S, NR, NC(O)R', NC(O)OR', NC(O)N(R')$_2$, or NS(O)$_2$R'.

X, Y, and Z are independently C, N, O, or S.

Each occurrence of R is independently hydrogen, halogen, cyano, $(C_1-C_8)$alkyl, $(C_2-C_8)$alkenyl, $(C_2-C_8)$alkynyl, $(C_1-C_8)$haloalkyl, $(C_1-C_8)$hydroxyhaloalkyl, $(C_1-C_8)$alkyl$(C_3-C_7)$cycloalkyl, $(C_1-C_8)$alkyl$(C_3-C_7)$heterocycloalkyl, $(C_1-C_8)$alkylaryl, $(C_1-C_8)$alkylheteroaryl, $(C_3-C_7)$cycloalkyl, $(C_3-C_7)$heterocycloalkyl, aryl, heteroaryl, —OR", —C(O)R', —C(O)OR', —OC(O)R', —OC(O)OR', —C(O)N(R')$_2$, —OC(O)N(R')$_2$, —N(R')$_2$, —NR'C(O)R', —NR'C(O)OR", —NR'C(O)N(R')$_2$, —NR' SO$_2$R", —SR", —S(O)R", —SO$_2$R", —S(O)$_2$OR", —SO$_2$N(R')$_2$, -L-OR", -L-C(O)R', -L-C(O)OR', -L-OC(O)R', -L-OC(O)N(R')$_2$, -L-N(R')$_2$, -L-NR'C(O)OR", -L-C(O)N(R')$_2$, -L-NR'C(O)R", -L-SR", -L-S(O)R", -L-SO$_2$R", -L-SO$_2$N(R')$_2$, or -L-NR'SO$_2$R".

Each occurrence of R' is independently hydrogen, $(C_1-C_8)$alkyl, $(C_2-C_8)$alkenyl, $(C_2-C_8)$alkynyl, $(C_1-C_8)$alkoxy$(C_1-C_8)$alkyl, $(C_1-C_8)$haloalkyl, $(C_1-C_8)$hydroxyalkyl, $(C_1-C_8)$hydroxyhaloalkyl, $(C_1-C_8)$alkyl$(C_3-C_7)$cycloalkyl, $(C_1-C_8)$alkyl$(C_3-C_7)$heterocycloalkyl, $(C_1-C_8)$alkylaryl, $(C_1-C_8)$alkylheteroaryl, $(C_3-C_7)$cycloalkyl, $(C_3-C_7)$heterocycloalkyl, aryl, or heteroaryl.

Alternatively, in some embodiments, two R' groups, when attached to the same nitrogen atom, can combine with the nitrogen atom to which they are attached to form a heterocyclic or heteroaryl group.

Each occurrence of R" is independently hydrogen, $(C_1-C_8)$ alkyl, $(C_2-C_8)$alkenyl, $(C_2-C_8)$alkynyl, $(C_1-C_8)$alkoxy$(C_1-C_8)$alkyl, $(C_1-C_8)$haloalkyl, $(C_1-C_8)$hydroxyalkyl, $(C_1-C_8)$hydroxyhaloalkyl, $(C_1-C_8)$alkyl$(C_3-C_7)$cycloalkyl, $(C_1-C_8)$alkyl$(C_3-C_7)$heterocycloalkyl, $(C_1-C_8)$alkylaryl, $(C_1-C_8)$alkylheteroaryl, $(C_3-C_7)$cycloalkyl, $(C_3-C_7)$heterocycloalkyl, aryl, or heteroaryl.

Any cycloalkyl portion, heterocycloalkyl portion, aryl portion, or heteroaryl portion is optionally substituted with one to four members selected from the group consisting of hydroxyl, halogen, cyano, nitro, $(C_1-C_8)$alkyl, $(C_2-C_8)$alkenyl, $(C_2-C_8)$alkynyl, $(C_1-C_8)$alkoxy, $(C_1-C_8)$haloalkyl, $(C_1-C_8)$hydroxyalkyl, $(C_1-C_8)$hydroxyhaloalkyl, —OR", —C(O)R', —C(O)OR', —OC(O)R', —OC(O)OR', —C(O)N(R')$_2$, —OC(O)N(R')$_2$, —N(R')$_2$, —NR'C(O)R', —NR'C(O)OR", —NR'C(O)N(R")$_2$, —NR'SO$_2$R", —SR", —S(O)R", —SO$_2$R", —S(O)$_2$OR", —SO$_2$N(R')$_2$, -L-OR", -L-C(O)R', -L-C(O)OR', -L-OC(O)R', -L-OC(O)N(R')$_2$, -L-N(R')$_2$, -L-NR'C(O)OR", -L-C(O)N(R')$_2$, -L-NR'C(O)R", -L-SR", -L-S(O)R", -L-SO$_2$R", -L-SO$_2$N(R')$_2$, and -L-NR'SO$_2$R".

L is $(C_1-C_8)$alkylene.

Variable m is an integer from 1 to 5, n is an integer from 0 to 2, and p is an integer from 0 to 11.

It should be understood that the following compounds are excluded from the scope of the present invention:

4-cyclohexyl-5-(3-fluorophenyl)-2-methyloxazole

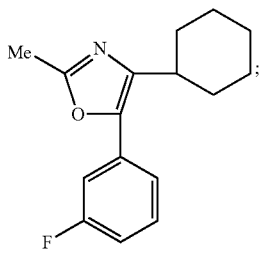 [SMILES: Cc1nc(C2CCCCC2)c(-c2cccc(F)c2)o1]

4-cyclohexyl-2-ethyl-5-(3-fluorophenyl)oxazole

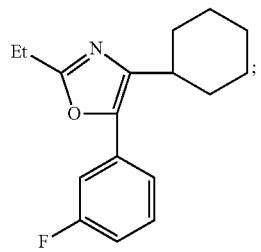 [SMILES: CCc1nc(C2CCCCC2)c(-c2cccc(F)c2)o1]

5-(4-chlorophenyl)-4-cyclopentyl-2-[(1S)-1-fluoroethyl]thiazole

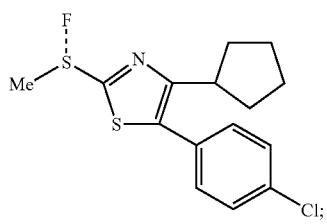

5-(4-chlorophenyl)-4-cyclohexyl-2-ethylthiazole

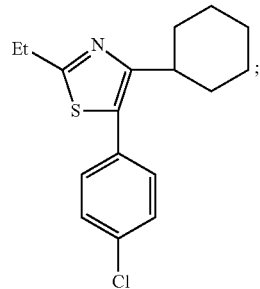 [SMILES: CCc1nc(C2CCCCC2)c(-c2ccc(Cl)cc2)s1]

4-cyclopentyl-2-ethyl-5-(4-ethylphenyl)thiazole

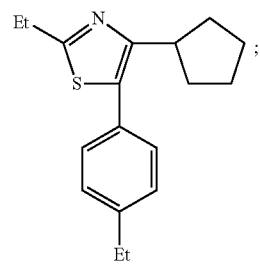

5-(3-chlorophenyl)-4-cyclopentyl-2-ethylthiazole

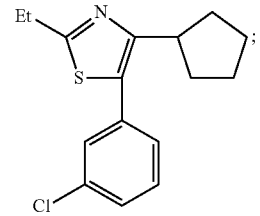 [SMILES: CCc1nc(C2CCCC2)c(-c2cccc(Cl)c2)s1]

4-cyclopentyl-2-ethyl-5-(3-methylphenyl)thiazole

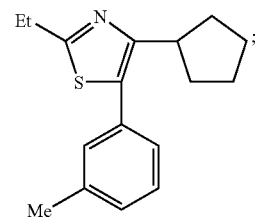 [SMILES: CCc1nc(C2CCCC2)c(-c2cccc(C)c2)s1]

5-(2-chlorophenyl)-4-cyclopentyl-2-ethylthiazole

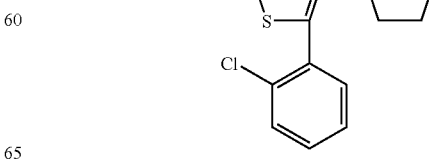

4-cyclopentyl-2-ethyl-5-(2-methylphenyl)thiazole

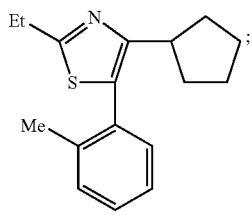 [SMILES: CCc1nc(C2CCCC2)c(-c2ccccc2C)s1]

4-cyclohexyl-5-(3-fluorophenyl)-2-methyloxazole

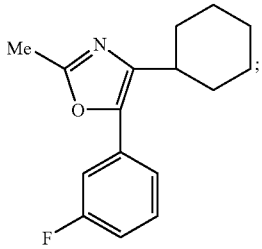 [SMILES: Cc1nc(C2CCCCC2)c(-c2cccc(F)c2)o1]

3-[4-(4-fluorophenyl)-2-methyl-5-thiazolyl]-1-pyrrolidinecarboxylic acid, ethyl ester

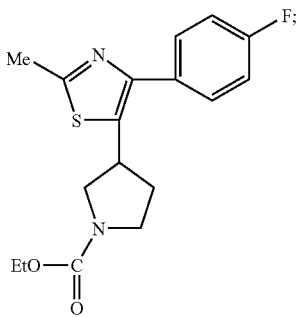 [SMILES: CCOC(=O)N1CCC(c2sc(C)nc2-c2ccc(F)cc2)C1]

4-(4-fluorophenyl)-2-methyl-5-(3-pyrrolidinyl)thiazole

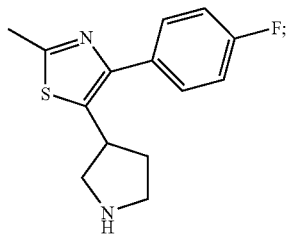 [SMILES: Cc1nc(-c2ccc(F)cc2)c(C2CCNC2)s1]

1-(4-fluorophenyl)-4-[3-[4-(4-fluorophenyl)-2-methyl-5-thiazolyl]-1-pyrrolidinyl]-1-butanone

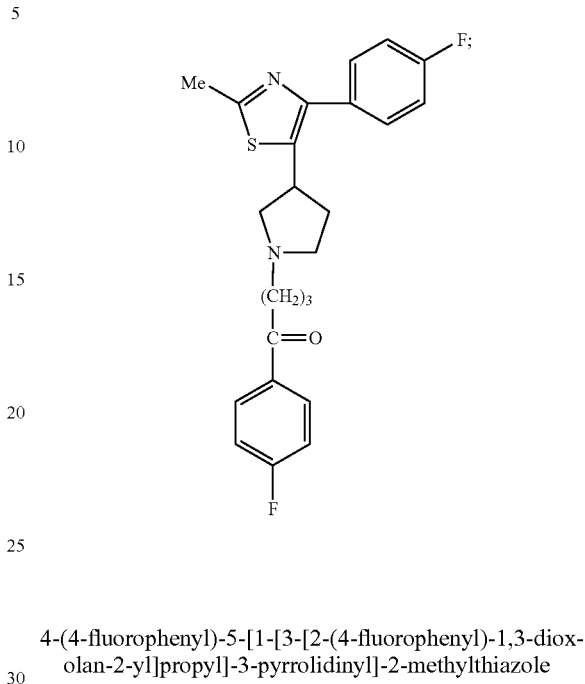

4-(4-fluorophenyl)-5-[1-[3-[2-(4-fluorophenyl)-1,3-dioxolan-2-yl]propyl]-3-pyrrolidinyl]-2-methylthiazole

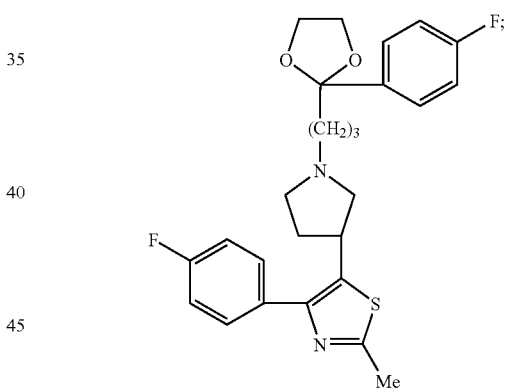

4-cyclohexyl-5-(3-fluorophenyl)-2-methyloxazole

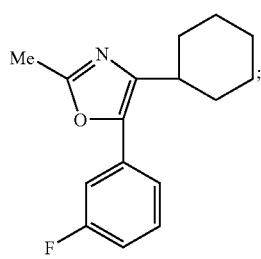 [SMILES: Cc1nc(C2CCCCC2)c(-c2cccc(F)c2)o1]

4-[5-cyclohexyl-2-(methylthio)-4-thiazolyl]-2,6-bis(1,1-dimethylethyl)phenol

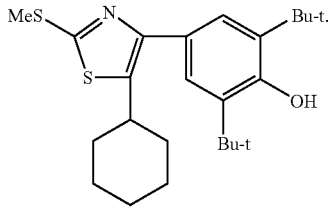

In one embodiment, optionally in combination with other embodiments herein described, at least one occurrence of R' is other than hydrogen.

In another embodiment, optionally in combination with other embodiments herein described, no occurrence of $R^1$ is —$SO_2NH_2$, —$SO_2$NH-alkyl, or —$SO_2$-alkyl.

In yet another embodiment, optionally in combination with other embodiments herein described, no occurrence of $R^2$ is —C(O)N(R')$_2$, hydroxyalkyl, alkoxyalkyl, or —$CO_2H$.

In a further embodiment, optionally in combination with other embodiments herein described, no occurrence of $R^3$ is hydroxyl, hydroxyalkyl, alkoxyalkyl, —$NH_2$, —NH-alkyl, aminoalkyl, —C(O)O-alkyl, —C(O)-alkyl, or -L-OC(O)-alkyl.

In still another embodiment, optionally in combination with other embodiments herein described, when X is S and Y is N, then no occurrence of $R^1$ is:
cyano or nitro;
—OR", —SR", hydroxyalkyl, or —OC(O)-alkyl;
—$NH_2$, —NHR', —N(alkyl)$_2$, —NR'C(O)R', —NR'C(O)OR", or —NR'C(O)N(R')$_2$; or
—C(O)-alkyl, —C(O)-aryl, —$CO_2H$, —C(O)O-alkyl, —C(O)N(R')$_2$, or -L-C(O)R'.

In another embodiment, optionally in combination with other embodiments herein described, m is 1, 2 or 3, and p is 0, 1 or 2.

In still another embodiment, optionally in combination with other embodiments herein described, m is 1 or 2, and p is 0 or 1.

In some embodiments, each occurrence of R' and $R^2$ is independently hydrogen, hydroxyl, halogen, nitro, cyano, ($C_1$-$C_8$)alkyl, ($C_1$-$C_8$)alkoxy, ($C_2$-$C_8$)alkenyl, ($C_2$-$C_8$)alkynyl, ($C_1$-$C_8$)haloalkyl, ($C_1$-$C_8$)hydroxyalkyl, ($C_1$-$C_8$)hydroxyhaloalkyl, ($C_1$-$C_8$)alkoxy($C_1$-$C_8$)alkyl, ($C_1$-$C_8$)alkyl($C_3$-$C_7$)cycloalkyl, ($C_1$-$C_8$)alkyl($C_3$-$C_7$)heterocycloalkyl, ($C_1$-$C_8$)alkylaryl, ($C_1$-$C_8$)alkylheteroaryl, ($C_3$-$C_7$)cycloalkyl, ($C_3$-$C_7$)heterocycloalkyl, aryl, heteroaryl, or —C(O)R'.

In other embodiments, each occurrence of $R^3$ is independently null, hydrogen, halogen, cyano, ($C_1$-$C_8$)alkyl, ($C_1$-$C_8$)alkoxy, ($C_2$-$C_8$)alkenyl, ($C_2$-$C_8$)alkynyl, ($C_1$-$C_8$)haloalkyl, ($C_1$-$C_8$)alkoxy($C_1$-$C_8$)alkyl, ($C_1$-$C_8$)alkyl($C_3$-$C_7$)cycloalkyl, ($C_1$-$C_8$)alkyl($C_3$-$C_7$)heterocycloalkyl, ($C_1$-$C_8$)alkylaryl, ($C_1$-$C_8$)alkylheteroaryl, ($C_3$-$C_7$)cycloalkyl, or ($C_3$-$C_7$)heterocycloalkyl.

In yet another embodiment, optionally in combination with other embodiments herein described, n is 0 or 1, and p is 0.

In some embodiments, each occurrence of $R^1$ is independently hydrogen, hydroxyl, halogen, ($C_1$-$C_8$)alkyl, ($C_1$-$C_8$) alkoxy, ($C_1$-$C_8$)haloalkyl, ($C_1$-$C_8$)hydroxyalkyl, ($C_1$-$C_8$)hydroxyhaloalkyl, ($C_1$-$C_8$)alkoxy($C_1$-$C_8$)alkyl, ($C_3$-$C_7$)cycloalkyl, ($C_3$-$C_7$)heterocycloalkyl, aryl, heteroaryl, or —C(O)R'.

In yet other embodiments, each occurrence of $R^3$ is independently null, hydrogen, halogen, ($C_1$-$C_8$)alkyl, ($C_1$-$C_8$) alkoxy, ($C_1$-$C_8$)haloalkyl, ($C_1$-$C_8$)alkoxy($C_1$-$C_8$)alkyl, ($C_3$-$C_7$)cycloalkyl, or ($C_3$-$C_7$)heterocycloalkyl.

In another embodiment, W is C(R)$_2$, O, NR, NC(O)R', or NS(O)$_2$R'.

In one embodiment, optionally in combination with other embodiments herein described, X is O, Z is N, and Y is C.

In another embodiment, optionally in combination with other embodiments herein described, X is N, Z is O, and Y is C.

In yet another embodiment, optionally in combination with other embodiments herein described, X is C, Z is N, and Y is O.

In still another embodiment, optionally in combination with other embodiments herein described, X is C, Z is O, and Y is N.

In yet another embodiment, optionally in combination with other embodiments herein described, X is N, Z is N, and Y is C. In one embodiment, $R^3$ attached to X is null and $R^3$ attached to Z is other than null. In another embodiment, $R^3$ attached to Z is null and $R^3$ attached to X is other than null.

In a further embodiment, optionally in combination with other embodiments herein described, X is C, Z is N, and Y is N. In one embodiment, $R^3$ attached to Z is null and $R^3$ attached to Y is other than null. In another embodiment, $R^3$ attached to Y is null and $R^3$ attached to Z is other than null.

In still another embodiment, optionally in combination with other embodiments herein described, X is O, Z is C, and Y is N.

In yet another embodiment, optionally in combination with other embodiments herein described, X is N, Z is C, and Y is O.

In a further embodiment, optionally in combination with other embodiments herein described, X is S, Z is C, and Y is N.

In another embodiment, optionally in combination with other embodiments herein described, X is N, Z is C, and Y is S.

In one embodiment, optionally in combination with other embodiments herein described, X is O, Z is N, Y is C, m is 2, n is 1, p is 0, and W is C(R)$_2$.

In another embodiment, optionally in combination with other embodiments herein described, X is O, Z is N, Y is C, m is 1, n is 1, p is 0, and W is C(R)$_2$, wherein R' is hydroxyhaloalkyl and at least one occurrence of R is aryl.

Compounds of formula (I) can have asymmetric centers and therefore exist in different enantiomeric or diastereomeric forms. The present invention relates to the use of all optical isomers and stereoisomers of compounds of formula (I), and mixtures thereof, and to all pharmaceutical compositions and methods of treatment that may employ or contain them.

It should be noted that racemates, racemic mixtures, and stereoisomers, particularly diastereomeric mixtures or diastereomerically pure compounds and enantiomers or enantiomerically pure compounds of the above, are all encompassed by the present invention.

Specific examples of compounds of formula (I) are provided below in Table 1:

TABLE 1
Examples of compounds of formula (I)
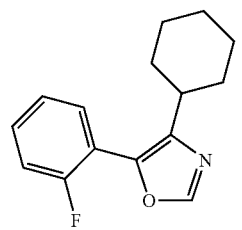 [SMILES: Fc1ccccc1-c1ocnc1C1CCCCC1]
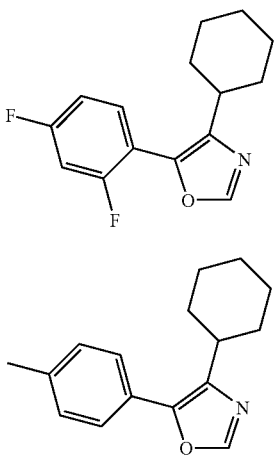
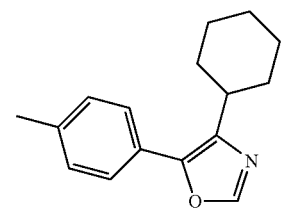 [SMILES: Cc1ccc(-c2ocnc2C2CCCCC2)cc1]
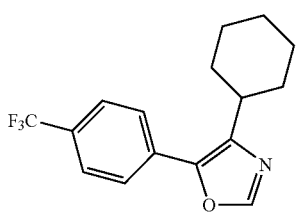 [SMILES: FC(F)(F)c1ccc(-c2ocnc2C2CCCCC2)cc1]
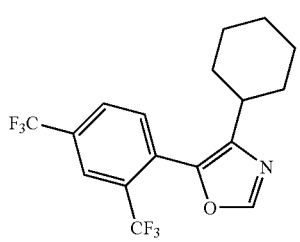 [SMILES: FC(F)(F)c1ccc(-c2ocnc2C2CCCCC2)c(C(F)(F)F)c1]
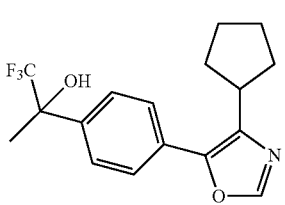 [SMILES: CC(O)(c1ccc(-c2ocnc2C2CCCC2)cc1)C(F)(F)F]
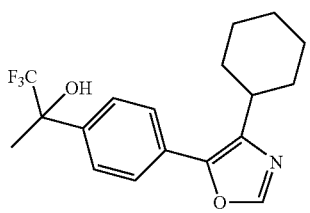 [SMILES: CC(O)(c1ccc(-c2ocnc2C2CCCCC2)cc1)C(F)(F)F]
TABLE 1-continued
Examples of compounds of formula (I)
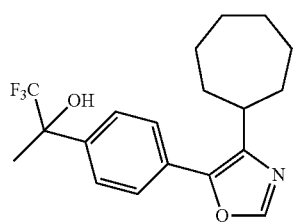 [SMILES: CC(O)(c1ccc(-c2ocnc2C2CCCCCC2)cc1)C(F)(F)F]
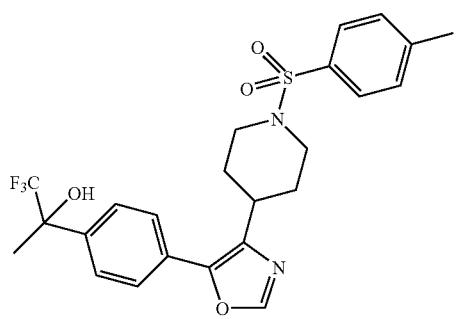 [SMILES: Cc1ccc(S(=O)(=O)N2CCC(c3ncoc3-c3ccc(C(C)(O)C(F)(F)F)cc3)CC2)cc1]
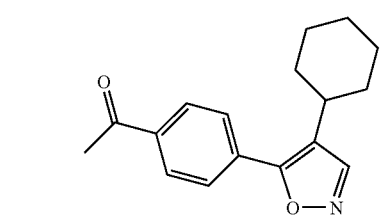 [SMILES: CC(=O)c1ccc(-c2oncc2C2CCCCC2)cc1]
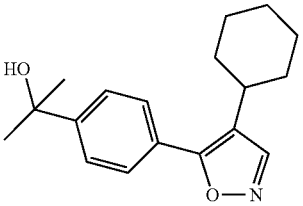 [SMILES: CC(C)(O)c1ccc(-c2oncc2C2CCCCC2)cc1]
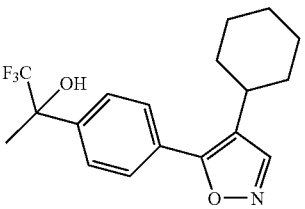 [SMILES: CC(O)(c1ccc(-c2oncc2C2CCCCC2)cc1)C(F)(F)F]
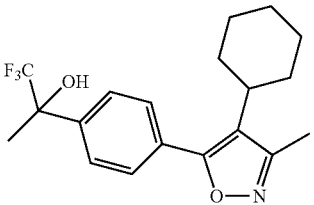 [SMILES: Cc1noc(-c2ccc(C(C)(O)C(F)(F)F)cc2)c1C1CCCCC1]

TABLE 1-continued

Examples of compounds of formula (I)

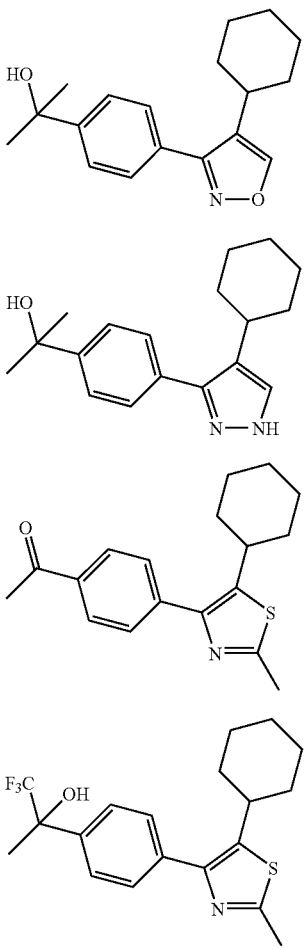

The present invention also provides tricyclic compounds of formula (I) that are in isolated and purified form.

The present invention further provides pharmaceutical compositions comprising a therapeutically effective amount of a tricyclic compound of formula (I) and a pharmaceutically acceptable vehicle, carrier, diluent or excipient.

In one embodiment, the pharmaceutical compositions comprise a tricyclic compound selected from Table 1 above.

Moreover, the present invention provides pharmaceutical compositions comprising a therapeutically effective amount of a tricyclic compound of formula (I) and one or more additional therapeutic agents.

In an embodiment, the pharmaceutical compositions comprise one or more additional therapeutic agents that are useful for treating a condition or disorder selected from the group consisting of diabetes, syndrome X, obesity, polycystic ovarian disease, an eating disorder, craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia, Cushing's syndrome, hypertension, atherosclerosis, vascular restenosis, retinopathy, nephropathy, neurodegenerative disease, neuropathy, muscle wasting, a cognitive disorder, dementia, depression, psoriasis, glaucoma, osteoporosis, a viral infection, an inflammatory disorder, and an immune disorder.

Further, the present invention provides a method for treating a condition or disorder selected from the group consisting of diabetes, syndrome X, obesity, polycystic ovarian disease, an eating disorder, craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia, Cushing's syndrome, hypertension, atherosclerosis, vascular restenosis, retinopathy, nephropathy, neurodegenerative disease, neuropathy, muscle wasting, a cognitive disorder, dementia, depression, psoriasis, glaucoma, osteoporosis, a viral infection, an inflammatory disorder, and an immune disorder, comprising administering to a patient in need thereof a therapeutically effective amount of a tricyclic compound of formula (I).

In one embodiment, the tricyclic compound is selected from Table I above.

In an embodiment, the invention provides a method for treating insulin-dependent diabetes mellitus, comprising administering to a patient in need thereof a therapeutically effective amount of a tricyclic compound of formula (I).

In another embodiment, the invention provides a method for treating non-insulin-dependent diabetes mellitus, comprising administering to a patient in need thereof a therapeutically effective amount of a tricyclic compound of formula (I).

In yet another embodiment, the invention provides a method for treating insulin resistance, comprising administering to a patient in need thereof a therapeutically effective amount of a tricyclic compound of formula (I).

In a further embodiment, the invention provides a method for treating obesity, comprising administering to a patient in need thereof a therapeutically effective amount of a tricyclic compound of formula (I).

The invention also provides a method for modulating cortisol production, comprising administering to a patient in need thereof a therapeutically effective amount of a tricyclic compound of formula (I).

Moreover, the invention provides a method for modulating hepatic glucose production, comprising administering to a patient in need thereof a therapeutically effective amount of a tricyclic compound of formula (I).

Furthermore, the invention provides a method for modulating hypothalamic function, comprising administering to a patient in need thereof a therapeutically effective amount of a tricyclic compound of formula (I).

The present invention also provides a method for treating a hydroxysteroid dehydrogenase-mediated condition or disorder, comprising administering to a patient in need thereof a therapeutically effective amount of a tricyclic compound of formula (I).

Furthermore, the invention provides a method for treating a condition or disorder responsive to modulation of a hydroxysteroid dehydrogenase, comprising administering to a patient in need thereof a therapeutically effective amount of a compound of formula (I).

In one embodiment, the hydroxysteroid dehydrogenase is 11β-HSD1.

The present invention also provides a method for modulating a hydroxysteroid dehydrogenase, comprising administering to a patient in need thereof a therapeutically effective amount of a tricyclic compound of formula (I).

Further, the invention provides a method for modulating the function of a hydroxysteroid dehydrogenase in a cell. In one embodiment, the cell is contacted with a tricyclic compound of formula (I). In another embodiment, a therapeutically effective amount of a tricyclic compound of formula (I)

is administered to a patient in need of such modulation. In a further embodiment, the tricyclic compound inhibits the hydroxysteroid dehydrogenase.

In one embodiment, the hydroxysteroid dehydrogenase is 11β-HSD1.

In an embodiment, the invention provides a method for treating an 11β-HSD1-mediated condition or disorder, comprising administering to a patient in need thereof a therapeutically effective amount of a tricyclic compound of formula (I).

In another embodiment, the invention provides a method for treating a condition or disorder responsive to modulation of 11β-HSD1, comprising administering to a patient in need thereof a therapeutically effective amount of a tricyclic compound of formula (I).

In yet another embodiment, the invention provides a method for modulating 11β-HSD1, comprising administering to a patient in need thereof a therapeutically effective amount of a tricyclic compound of formula (I).

In a further embodiment, the invention provides a method for modulating the function of 11β-HSD1 in a cell, comprising administering to a patient in need thereof a therapeutically effective amount of a tricyclic compound of formula (I).

In an embodiment, the invention provides a method for treating an 11β-HSD2-mediated condition or disorder, comprising administering to a patient in need thereof a therapeutically effective amount of a tricyclic compound of formula (I).

In another embodiment, the invention provides a method for treating a condition or disorder responsive to modulation of 11β-HSD2, comprising administering to a patient in need thereof a therapeutically effective amount of a tricyclic compound of formula (I).

In yet another embodiment, the invention provides a method for modulating 11β-HSD2, comprising administering to a patient in need thereof a therapeutically effective amount of a tricyclic compound of formula (I).

In still another embodiment, the invention provides a method for modulating the function of 11β-HSD2 in a cell, comprising administering to a patient in need thereof a therapeutically effective amount of a tricyclic compound of formula (I).

In an embodiment, the invention provides a method for treating an 17β-HSD3-mediated condition or disorder, comprising administering to a patient in need thereof a therapeutically effective amount of a tricyclic compound of formula (I).

In another embodiment, the invention provides a method for treating a condition or disorder responsive to modulation of 17β-HSD3, comprising administering to a patient in need thereof a therapeutically effective amount of a tricyclic compound of formula (I).

In a further embodiment, the invention provides a method for modulating 17β-HSD3, comprising administering to a patient in need thereof a therapeutically effective amount of a tricyclic compound of formula (I).

In yet another embodiment, the invention provides a method for modulating the function of 17β-HSD3 in a cell, comprising administering to a patient in need thereof a therapeutically effective amount of a tricyclic compound of formula (I).

The present invention also relates to the use of a compound of formula (I) according to any one of the above embodiments in the preparation of a medicament. In one embodiment, the medicament comprises a compound of formula (I) according to any one of the above embodiments and a pharmaceutically acceptable vehicle, carrier, excipient, or diluent.

Further, the present invention relates to the use of a compound of formula (I) according to any one of the above embodiments in the preparation of a medicament for treating a hydroxysteroid dehydrogenase-mediated condition or disorder, the medicament comprising the compound of formula (I) and a pharmaceutically acceptable vehicle, carrier, excipient, or diluent.

In an embodiment, the invention relates to the use of a compound of formula (I) according to any one of the above embodiments in the preparation of a medicament for treating a condition or disorder mediated by 11β-HSD1, 11β-HSD2 or 17β-HSD3, the medicament comprising the compound of formula (I) and a pharmaceutically acceptable carrier.

Moreover, the present invention relates to the use of a compound of formula (I) according to any one of the above embodiments in the preparation of a medicament for treating a condition or disorder responsive to modulation of a hydroxysteroid dehydrogenase, the medicament comprising the compound of formula (I) and a pharmaceutically acceptable vehicle, carrier, excipient, or diluent.

In an embodiment, the invention relates to the use of a compound of formula (I) according to any one of the above embodiments in the preparation of a medicament for treating a condition or disorder responsive to modulation of 11β-HSD1, 11β-HSD2 or 17β-HSD3, the medicament comprising the compound of formula (I) and a pharmaceutically acceptable carrier.

Furthermore, the present invention relates to the use of a compound of formula (I) according to any one of the above embodiments in the preparation of a medicament for the treatment of diabetes, syndrome X, obesity, polycystic ovarian disease, an eating disorder, craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia, Cushing's syndrome, hypertension, atherosclerosis, vascular restenosis, retinopathy, nephropathy, neurodegenerative disease, neuropathy, muscle wasting, a cognitive disorder, dementia, depression, psoriasis, glaucoma, osteoporosis, a viral infection, an inflammatory disorder, or an immune disorder, the medicament comprising the compound of formula (I) and a pharmaceutically acceptable vehicle, carrier, excipient, or diluent.

One embodiment of the invention relates to the use of a compound of formula (I) according to any one of the above embodiments in the preparation of a medicament for the treatment of diabetes, the medicament comprising the compound of formula (I) and a pharmaceutically acceptable carrier.

Another embodiment of the invention relates to the use of a compound of formula (I) according to any one of the above embodiments in the preparation of a medicament for the treatment of insulin-dependent diabetes mellitus, the medicament comprising the compound of formula (I) and a pharmaceutically acceptable carrier.

A further embodiment of the invention relates to the use of a compound of formula (I) according to any one of the above embodiments in the preparation of a medicament for the treatment of non-insulin-dependent diabetes mellitus, the medicament comprising the compound of formula (I) and a pharmaceutically acceptable carrier.

Yet another embodiment of the invention relates to the use of a compound of formula (I) according to any one of the above embodiments in the preparation of a medicament for the treatment of insulin resistance, the medicament comprising the compound of formula (I) and a pharmaceutically acceptable carrier.

An embodiment of the invention relates to the use of a compound of formula (I) according to any one of the above embodiments in the preparation of a medicament for the treatment of obesity, the medicament comprising the compound of formula (I) and a pharmaceutically acceptable carrier.

Another embodiment of the invention relates to the use of a compound of formula (I) according to any one of the above embodiments in the preparation of a medicament for modulating cortisol production, the medicament comprising the compound of formula (I) and a pharmaceutically acceptable carrier.

Yet another embodiment of the invention relates to the use of a compound of formula (I) according to any one of the above embodiments in the preparation of a medicament for modulating hepatic glucose production, the medicament comprising the compound of formula (I) and a pharmaceutically acceptable carrier.

A further embodiment of the invention relates to the use of a compound of formula (I) according to any one of the above embodiments in the preparation of a medicament for modulating hypothalamic function, the medicament comprising the compound of formula (I) and a pharmaceutically acceptable carrier.

One embodiment of the invention relates to the use of a compound of formula (I) according to any one of the above embodiments in the preparation of a medicament for modulating a hydroxysteroid dehydrogenase, the medicament comprising the compound of formula (I) and a pharmaceutically acceptable carrier.

Another embodiment of the invention relates to the use of a compound of formula (I) according to any one of the above embodiments in the preparation of a medicament for modulating 11β-HSD1, 11β-HSD2 or 17β-HSD3, the medicament comprising the compound of formula (I) and a pharmaceutically acceptable carrier.

Yet another embodiment of the invention relates to the use of a compound of formula (I) according to any one of the above embodiments in the preparation of a medicament for modulating the function of a hydroxysteroid dehydrogenase, the medicament comprising the compound of formula (I) and a pharmaceutically acceptable carrier.

Still another embodiment of the invention relates to the use of a compound of formula (I) according to any one of the above embodiments in the preparation of a medicament for modulating the function of 11β-HSD1, 111β-HSD2 or 17β-HSD3, the medicament comprising the compound of formula (I) and a pharmaceutically acceptable carrier.

A further embodiment of the invention relates to the use of a compound of formula (I) according to any one of the above embodiments in the preparation of a medicament for the inhibition of a hydroxysteroid dehydrogenase, the medicament comprising the compound of formula (I) and a pharmaceutically acceptable carrier.

Yet another embodiment of the invention relates to the use of a compound of formula (I) according to any one of the above embodiments in the preparation of a medicament for the inhibition of 11β-HSD1, 11β-HSD2 or 17β-HSD3, the medicament comprising the compound of formula (I) and a pharmaceutically acceptable carrier.

The present invention also relates to the manufacture of a medicament comprising a compound of formula (I) according to any one of the above embodiments.

Further, the present invention relates to a method of manufacturing a medicament comprising a compound of formula (I) according to any one of the above embodiments, the method comprising combining the compound of formula (I) with a pharmaceutically acceptable vehicle, carrier, excipient, or diluent to form the medicament.

In one embodiment, the invention relates to a method of manufacturing a medicament for treating a hydroxysteroid dehydrogenase-mediated condition or disorder, the method comprising combining a compound of formula (I) according to any one of the above embodiments with a pharmaceutically acceptable carrier to form the medicament.

In another embodiment, the invention relates to a method of manufacturing a medicament for treating a condition or disorder responsive to modulation of a hydroxysteroid dehydrogenase, the method comprising combining a compound of formula (I) according to any one of the above embodiments with a pharmaceutically acceptable carrier to form the medicament.

In a further embodiment, the invention relates to a method of manufacturing a medicament for the treatment of diabetes, syndrome X, obesity, polycystic ovarian disease, an eating disorder, craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia, Cushing's syndrome, hypertension, atherosclerosis, vascular restenosis, retinopathy, nephropathy, neurodegenerative disease, neuropathy, muscle wasting, a cognitive disorder, dementia, depression, psoriasis, glaucoma, osteoporosis, a viral infection, an inflammatory disorder, or an immune disorder, the method comprising combining a compound of formula (I) according to any one of the above embodiments with a pharmaceutically acceptable carrier to form the medicament.

In yet another embodiment, the invention relates to a method of manufacturing a medicament for modulating a hydroxysteroid dehydrogenase, the method comprising combining a compound of formula (I) according to any one of the above embodiments with a pharmaceutically acceptable carrier to form the medicament.

In still another embodiment, the invention relates to a method of manufacturing a medicament for modulating the function of a hydroxysteroid dehydrogenase, the method comprising combining a compound of formula (I) according to any one of the above embodiments with a pharmaceutically acceptable carrier to form the medicament.

In a further embodiment, the invention relates to a method of manufacturing a medicament for the inhibition of a hydroxysteroid dehydrogenase, the method comprising combining a compound of formula (I) according to any one of the above embodiments with a pharmaceutically acceptable carrier to form the medicament.

Pharmaceutical Compositions

Pharmaceutical compositions and single unit dosage forms comprising a tricyclic compound, or a pharmaceutically acceptable stereoisomer, prodrug, salt, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton, Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous (e.g., <1% water) pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The tricyclic compounds can be administered to a mammal (e.g., human, mouse, rat, rabbit, dog, cat, bovine, pig, monkey) as 11β-HSD1 modulators, prophylactic or therapeutic drugs of diabetes, prophylactic or therapeutic drugs of diabetic complications (e.g., retinopathy, nephropathy, neuropathy, cardiac infarction, and cerebral infarction based on arteriosclerosis), prophylactic or therapeutic drugs of hyperlipemia, prophylactic or therapeutic drugs of obesity, neurodegenerative diseases and the like, or prophylactic or therapeutic drugs of diseases mediated by 11β-HSD1.

The tricyclic compounds can be administered to a mammal concurrently with one or more additional therapeutic agents for the treatment of a disease, such as diabetes or obesity, with the aim of the prophylaxis or treatment of a disease. As such, the tricyclic compounds of the present invention can be administered in combination with other therapeutic agents for the treatment or prevention of numerous diseases, including, but not limited to, diabetes and obesity.

Depending on the disease to be treated and the patient's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the case of a combined administration, the tricyclic compounds may be administered simultaneously with one or more additional therapeutic agents that are useful for the treatment or prevention of diabetes, obesity or other disease, or may be administered at a time prior to or subsequent to other therapeutic agent(s). In the case of combined administration, a pharmaceutical composition containing the tricyclic compound and one or more additional therapeutic agents can be administered. Alternatively, a pharmaceutical composition containing the tricyclic compound and a pharmaceutical composition containing one or more additional therapeutic agents may be administered separately. The administration routes of respective pharmaceutical compositions may be the same or different.

In the case of a combined administration, the tricyclic compounds may be administered at a dose of 50 mg to 800 mg per administration, which may be given once to several times a day or less frequently (e.g., once weekly). In addition, the compound may be administered at a smaller dose. The combined pharmaceutical agent can be administered at a dose generally employed for the prophylaxis or treatment of diabetes or obesity or at a smaller dose than that.

Like the amounts and types of excipients, the amounts and specific types of active ingredients in a dosage form may differ depending on factors such as, but not limited to, the route by which they are to be administered to patients. However, typical dosage forms of the invention comprise a tricyclic compound, or a pharmaceutically acceptable salt, solvate, clathrate, hydrate, polymorph or prodrug thereof. In the treatment or prevention of diabetes, obesity, glaucoma, osteoporosis, cognitive disorders, immune disorders, depression or other conditions or disorders associated with the modulation of an hydroxysteroid dehydrogenase, an appropriate dosage level will generally be from about 0.001 to about 100 mg per kg patient body weight per day which can be administered in single or multiple doses. An exemplary dosage level will be from about 0.01 to about 25 mg/kg per day or about 0.05 to about 10 mg/kg per day. In other embodiments, a suitable dosage level may be from about 0.01 to about 25 mg/kg per day, about 0.05 to about 10 mg/kg per day, or about 0.1 to about 5 mg/kg per day. Within this range the dosage may be from about 0.005 to about 0.05, from about 0.05 to about 0.5, or from about 0.5 to about 5.0 mg/kg per day, which lie within the range of from about 0.1 mg to about 2000 mg per day, and which may be given as a single once-a-day dose in the morning or as divided doses throughout the day taken with food. In one embodiment, the daily dose is administered twice daily in equally divided doses. A daily dose range can be from about 5 mg to about 500 mg per day, or between about 10 mg and about 300 mg per day. In managing the patient, the therapy can be initiated at a lower dose, perhaps from about 1 mg to about 25 mg, and increased if necessary up to from about 200 mg to about 2000 mg per day as either a single dose or divided doses, depending on the patient's global response.

For multidrug therapy, the weight ratio of the compound of the invention to the second active ingredient may be varied and will depend upon the effective dose of each ingredient. Generally, an effective dose of each will be used. Thus, for example, when a compound of the invention is combined with an NSAID, the weight ratio of the compound of the invention to the NSAID will generally range from about 1000:1 to about 1:1000, such as about 200:1 to about 1:200. Combinations of a compound of the invention and other active ingredients generally will also be within the aforementioned range, but in each case, an effective dose of each active ingredient should be used.

It will be understood, however, that the specific dose level and frequency of dosage for any particular patient may be varied and will depend upon a variety of factors including: the activity of the specific compound employed; the metabolic stability and length of action of that compound; the age, body weight, general health, sex, and diet of the patient; mode and time of administration; rate of excretion; drug combination; the severity of the particular condition, and the host undergoing therapy.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton, Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, e.g., a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

For oral administration, the compositions can be provided in the form of tablets containing about 1 to about 1000 milligrams of the active ingredient. In other embodiments, the compositions are provided in the form of tablets containing about 1.0, about 5.0, about 10.0, about 15.0. about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, or about 1000.0 milligrams of the active ingredient for the symptomatic adjustment of the dosage to the patient to be treated. The compounds may be administered on a regimen of 1 to 4 times per day, such as, e.g., once or twice per day.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide slow or controlled-release of one or more active ingredients using, e.g., hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

Controlled-release pharmaceutical products can improve drug therapy over that achieved by their non-controlled counterparts. Ideally, the use of an optimally designed controlled-release preparation in medical treatment is characterized by a minimum amount of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms can be sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. For example, lyophilized sterile compositions suitable for reconstitution into particulate-free dosage forms are suitable for administration to humans.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Parenteral dosage forms are exemplary for the methods of preventing, treating or managing disease in a cancer patient.

Transdermal and Topical Dosage Forms

Transdermal and topical dosage forms of the invention include, but are not limited to, creams, lotions, ointments, gels, solutions, emulsions, suspensions, or other forms known to one of skill in the art. See, e.g., Remington's Pharmaceutical Sciences, 18th eds., Mack Publishing, Easton, Pa. (1990); and Introduction to Pharmaceutical Dosage Forms, 4th ed., Lea & Febiger, Philadelphia, Pa. (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane- 1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants also can be added to pharmaceutical compositions and dosage forms if desired. Examples of such additional ingredients are well known in the art. See, e.g., Remington's Pharmaceutical Sciences, 18th eds., Mack Publishing, Easton, Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Mucosal Dosage Forms and Lung Delivery

Mucosal dosage forms of the invention include, but are not limited to, ophthalmic solutions, sprays and aerosols, or other forms known to one of skill in the art. See, e.g., Remington's Pharmaceutical Sciences, 18th eds., Mack Publishing, Easton, Pa. (1990); and Introduction to Pharmaceutical Dosage Forms, 4th ed., Lea & Febiger, Philadelphia, Pa. (1985). Dosage forms suitable for treating mucosal tissues within the oral cavity can be formulated as mouthwashes or as oral gels. In one embodiment, the aerosol comprises a carrier. In another embodiment, the aerosol is carrier free.

A compound of the invention can also be administered directly to the lung by inhalation (see, e.g., Tong et al., International Publication No. WO 97/39745, and Clark et al, International Publication No. WO 99/47196, which are herein incorporated by reference). For administration by inhalation, a tricyclic compound can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a tricyclic compound directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a tricyclic compound to the lung (see, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a tricyclic compound to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a tricyclic compound to the lung. Nebulizers create aerosols from liquid drug formulations by using, for example, ultrasonic energy to form fine particles that can be readily inhaled (see e.g., Verschoyle et al., British J Cancer, 1999, 80, Suppl 2, 96, which is herein incorporated by reference). Examples of nebulizers include devices supplied by Sheffield/Systemic Pulmonary Delivery Ltd. (see Armer et al., U.S. Pat. No. 5,954,047; van der Linden et al., U.S. Pat. No. 5,950,619; and van der Linden et al., U.S. Pat. No. 5,970,974, all of which are herein incorporated by reference), Aventis, and Batelle Pulmonary Therapeutics. Inhaled compounds, delivered by nebulizer devices, are currently under investigation as treatments for aerodigestive cancer (Engelke et al., Poster 342 at American Association of Cancer Research, San Francisco, Calif., Apr. 1-5, 2000) and lung cancer (Dahl et al., Poster 524 at American Association of Cancer Research, San Francisco, Calif., Apr. 1-5, 2000).

In one embodiment, an electrohydrodynamic ("EHD") aerosol device is used to deliver a tricyclic compound to the lung. EHD aerosol devices use electrical energy to aerosolize liquid drug solutions or suspensions (see, e.g., Noakes et al., U.S. Pat. No. 4,765,539; Coffee, U.S. Pat. No. 4,962,885; Coffee, International Publication No. WO 94/12285; Coffee, International Publication No. WO 94/14543; Coffee, International Publication No. WO 95/26234; Coffee, International Publication No. WO 95/26235; and Coffee, International Publication No. WO 95/32807, all of which are herein incorporated by reference). The electrochemical properties of the compound of the invention formulation may be important parameters to optimize when delivering this drug to the lung with an EHD aerosol device and such optimization is routinely performed by one of skill in the art. EHD aerosol devices may more efficiently deliver drugs to the lung than existing pulmonary delivery technologies. Other methods of intra-pulmonary delivery of a tricyclic compound will be known to the skilled artisan and are within the scope of the invention.

Liquid drug formulations suitable for use with nebulizers and liquid spray devices and EHD aerosol devices will typically include a tricyclic compound with a pharmaceutically acceptable carrier. For instance, the pharmaceutically acceptable carrier is a liquid such as an alcohol, water, polyethylene glycol or a perfluorocarbon. Optionally, another material can be added to alter the aerosol properties of the solution or suspension of a tricyclic compound. In some embodiments, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. Nos. 5,112,598, and Biesalski, 5,556,611, which are herein incorporated by reference). A compound of the invention can also be formulated in rectal or vaginal compositions such as suppositories or retention enemas, e.g., containing conventional suppository bases such as cocoa butter or other glycerides.

In addition to the formulations described previously, a tricyclic compound can also be formulated as a depot preparation. Such long acting formulations can be administered by implantation (e.g., subcutaneously or intramuscularly) or by intramuscular injection. Thus, e.g., the compounds can be formulated with suitable polymeric or hydrophobic materials (e.g., as an emulsion in an acceptable oil) or ion exchange resins, or as sparingly soluble derivatives, e.g., as a sparingly soluble salt.

Other Delivery Systems

Alternatively, other pharmaceutical delivery systems can be employed. Liposomes and emulsions are well known examples of delivery vehicles that can be used to deliver a tricyclic compound. Certain organic solvents such as dimethylsulfoxide can also be employed, although possibly at the risk of greater toxicity. A compound of the invention can also be delivered in a controlled release system. In one embodiment, a pump can be used (Sefton, CRC Crit. Ref. Biomed. Eng., 1987, 14, 201; Buchwald et al., Surgery, 1980, 88, 507; Saudek et al., New Engl. J. Med., 1989, 321, 574). In another embodiment, polymeric materials can be used (see Medical Applications of Controlled Release, Langer and Wise (eds.), CRC Press, Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem., 1983, 23, 61; see also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see, e.g., Langer, Science, 1990, 249, 1527).

Suitable excipients (e.g., carriers and diluents) and other materials that can be used to provide mucosal dosage forms encompassed by this invention are well known to those skilled in the pharmaceutical arts, and depend on the particular site to which or on the method by which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton, Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Therapeutic Uses of the Tricyclic Compounds

In one embodiment, the invention provides a method for treating or preventing a condition or disorder associated with the modulation of a hydroxysteroid dehydrogenase by administering to a patient having such a condition or disorder a therapeutically effective amount of a compound or composition of the invention. In one group of embodiments, conditions and disorders, including chronic diseases of humans or other species, can be treated with modulators, stimulators, or inhibitors of hydroxysteroid dehydrogenases, such as 11β-HSD1.

Treatment or Prevention of Diabetes

Diabetes and diabetic conditions can be treated or prevented by administration of a therapeutically effective amount of a tricyclic compound.

Types of diabetes that can be treated or prevented by administering a therapeutically effective amount of a tricyclic compound include type I diabetes mellitus (juvenile onset diabetes, insulin dependent-diabetes mellitus (IDDM)), type II diabetes mellitus (non-insulin-dependent diabetes mellitus (NIDDM)), insulinopathies, diabetes associated with pancreatic disorders, diabetes associated with other disorders (such as Cushing's Syndrome, acromegaly, pheochromocytoma, glucagonoma, primary aldosteronism, and somatostatinoma), type A and type B insulin resistance syndromes, lipatrophic diabetes, and diabetes induced by β-cell toxins.

In one embodiment, the type of diabetes being treated is type II diabetes.

Treatment or Prevention of Obesity

Obesity can be treated or prevented by administration of a therapeutically effective amount of a tricyclic compound.

Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Metabolic disorders, such as hyperlidemia and diabetes, and cardiovascular disorders, such as hypertension and coronary artery disease, are commonly associated with obesity.

Complications due to obesity may also be treated or prevented by administering a therapeutically effective amount of a tricyclic compound. Such complications include, but are not limited to, sleep apnea, Pickwickian syndrome, orthopedic disturbances of weight-bearing and non-weight-bearing joints, and skin disorders resulting from increased sweat or skin secretions.

Treatment or Prevention of Other Conditions

Other conditions that can be treated or prevented by administering a therapeutically effective amount of a tricyclic compound include, but are not limited to any condition which is responsive to the modulation, such as inhibition, of a hydroxysteroid dehydrogenase or a specific isoform thereof, and which thereby benefits from administration of such a modulator. Representative conditions in this regard include, but are not limited to, metabolic disorders and related cardiovascular risk factors such as syndrome X, polycystic ovarian disease, eating disorders (e.g., anorexia and bulimia), craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia and Cushing's syndrome; diseases associated therewith such as hypertension, atherosclerosis, vascular restenosis, retinopathy and nephropathy; neurologic disorders such as neurodegenerative disease, neuropathy and muscle wasting; cognitive disorders such as age-related learning disorders, dementia, neurodegeneration, as well as disorders of cognitive function in subjects ranging from the severely impaired (e.g., Parkinsons's or Alzheimer's associated dementia) to mildly impaired (e.g., age-associated memory impairment, drug-induced cognitive impairment) (see Sandeep et al., PNAS, electronically available at www.pnas.org/cgi/doi/10.1073/pnas.0306996101); androgen and/or estrogen-related disorders such as prostate cancer, colon cancer, breast cancer, benign prostatic hyperplasia, ovarian cancer, uterine cancer, and male pseudohermaphrodism; endometriosis; depression; psoriasis; glaucoma; osteoporosis; viral infections; inflammatory disorders; and immune disorders. The compounds of the invention may also improve the cognitive function of unimpaired subjects (e.g., serve as cognitive enhancers for the general population).

Additional Therapeutic Agents

In one embodiment, the present method for treating or preventing further comprises the administration of a therapeutically effective amount of one or more additional therapeutic agents useful for treating or preventing the diseases or disorders disclosed herein. In this embodiment, the time in which the therapeutic effect of the other therapeutic agent(s) is exerted overlaps with the time in which the therapeutic effect of the tricyclic compound is exerted.

The compounds of the invention can be combined or used in combination with other agents useful in the treatment, prevention, suppression or amelioration of the conditions or disorders for which compounds of the invention are useful, including diabetes, obesity, glaucoma, osteoporosis, cognitive disorders, immune disorders, depression and those pathologies noted above.

Such other agents, or drugs, may be administered, by a route and in an amount commonly used therefor, simultaneously or sequentially with a tricyclic compound. In one embodiment, a pharmaceutical composition contains one or more such other agents or drugs in addition to the compound of the invention when a tricyclic compound is used contemporaneously with one or more other agents or drugs. Accordingly, the pharmaceutical compositions of the invention include those that also contain one or more other active ingredients or therapeutic agents, in addition to a tricyclic compound.

In an embodiment, for the treatment or prevention of diabetes, a tricyclic compound can be administered with one or more additional therapeutic agents including, but not limited to, anti-diabetic agents such as insulin, inhaled insulin (Exubera®), insulin mimetics, insulin secretogues, sulfonylureas (e.g., glyburide, meglinatide, glimepiride, gliclazide, glipizide, gliquidone, chloropropresponsivemide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide), biguanides (e.g., metformin (Glucophage®)), α-glucosidase inhibitors (e.g., acarbose, voglibose and miglitol), thiazolidinone compounds (e.g., rosiglitazone (Avandia®), troglitazone (Rezulin®), ciglitazone, pioglitazone (Actos®) and englitazone), prandial glucose regulators (e.g., repaglinide and nateglinide), and glucagon receptor antagonists.

In another embodiment, for the treatment or prevention of obesity, a tricyclic compound can be administered with one or more additional therapeutic agents, including, but not limited to, β3 adrenergic receptor agonists, leptin or derivatives thereof, neuropeptide Y (e.g., NPY5) antagonists, and mazindol.

Examples of other therapeutic agents that may be combined with a tricyclic compound, either administered separately or in the same pharmaceutical composition, include, but are not limited to: (i) cholesterol-lowering agents such as HMG-CoA reductase inhibitors (e.g., lovastatin, simvastatin (Zocor®), pravastatin, fluvastatin, atorvastatin (Lipitor®) and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; (ii) antithrombotic agents such as thrombolytic agents (e.g., streptokinase, alteplase, anistreplase and reteplase), heparin, hirudin and warfarin derivatives, β-blockers (e.g., atenolol), β adrenergic agonists (e.g., isoproterenol), angiotensin II antagonists, ACE inhibitors and vasodilators (e.g., sodium nitroprusside, nicardipine hydrochloride, nitroglycerin and enaloprilat); (iii) PPAR agonists (e.g., $PPAR_\gamma$ and $PPAR_\delta$ agonists); (iv) DP antagonists; (v) lubricants or emollients such as petrolatum and lanolin, keratolytic agents, vitamin $D_3$ derivatives (e.g., calcipotriene and calcipotriol (Dovonex®)), PUVA, anthralin (Drithrocreme®), etretinate (Tegison®) and isotretinoin; (vi) glaucoma therapies such as cholinergic agonists (e.g., pilocarpine and carbachol), cholinesterase inhibitors (e.g., physostigmine, neostigmine, demacarium, echothiophate iodide and isofluorophate), carbonic anhydrase inhibitors (e.g., acetazolamide, dichlorphenamide, methazolamide, ethoxzolamide and dorzolamide), non-selective adrenergic agonists (e.g., epinephrine and dipivefrin), $\alpha_2$-selective adrenergic agonists (e.g., apraclonidine and brimonidine), β-blockers (e.g., timolol, betazolol, levobunolol, carteolol and metipranolol), prostaglandin analogs (e.g., latanoprost) and osmotic diuretics (e.g., glycerin, mannitol and isosorbide); corticosteroids such as beclomethasone, methylprednisolone, betamethasone, prednisone, prenisolone, dexamethasone, fluticasone and hydrocortisone, and corticosteroid analogs such as budesonide; (vii) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolates (e.g., mycophenolate mofetil (CellCepte®); (viii) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetylsalicylic acid and sulfasalazine), and pyrazolones (e.g., apazone, bezpiperylon, feprazone, mofebutazone, oxyphenbutazone and phenylbutazone); (ix) cyclooxygenase-2 (COX-2) inhibitors such as celecoxib (Celebrex®) and rofecoxib (Vioxx®); (xi) inhibitors of phosphodiesterase type IV (PDE-IV); (xii) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (xiii) hepatoprotective agents; and (xiv) other compounds such as 5-aminosalicylic acid and prodrugs thereof.

The weight ratio of the compound of the invention to one or more additional active ingredients may be varied and will depend upon the effective dose of each ingredient. Generally, an effective dose of each will be used. Thus, for example, when a tricyclic compound is combined with an NSAID, the weight ratio of the compound of the invention to the NSAID will generally range from about 1000:1 to about 1:1000, such as, e.g., about 200:1 to about 1:200. Combinations of a tricyclic compound and one or more additional active ingredients will generally also be within the aforementioned range, but in each case, an effective dose of each active ingredient should be used.

Kits

The invention encompasses kits that can simplify the administration of a tricyclic compound, or composition thereof, to a patient.

A typical kit of the invention comprises a unit dosage of a tricyclic compound. In one embodiment, the unit dosage form is in a container, which can be sterile, containing a therapeutically effective amount of a tricyclic compound and a pharmaceutically acceptable vehicle. In another embodiment, the unit dosage form is in a container containing a therapeutically effective amount of a tricyclic compound as a lyophilate or pharmaceutically acceptable salt. In this instance, the kit can further comprise another container that contains a solution useful for the reconstitution of the lyophilate or dissolution of the salt. The kit can also comprise a label or printed instructions for use of the tricyclic compound.

In a further embodiment, the kit comprises a unit dosage form of a composition of the invention.

Kits of the invention can further comprise one or more devices that are useful for administering the unit dosage forms of a tricyclic compound, or a composition thereof. Examples of such devices include, but are not limited to, a syringe, a drip bag, a patch or an enema, which optionally contain the unit dosage forms.

The present invention is not to be limited in scope by the specific embodiments disclosed in the examples, which are intended as illustrations of a few embodiments of the invention, and any embodiments that are functionally equivalent are within the scope of this invention. Indeed, various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence.

Preparation of Tricyclic Compounds of Formula (I)

Representative synthetic schemes, methods, reactions, reagents, and reaction conditions for the preparation of compounds of formula (I) are described below. Those skilled in the art will recognize that there are a variety of synthetic schemes, methods, reactions, reagents, and reaction conditions available to synthesize compounds of formula (I) described herein and represented in the claims.

To facilitate a reaction or the formation of particular functional groups, or to avoid undesired side reactions, protecting (or "blocking") groups may be employed. The use of protecting groups to protect functional groups from undesired side reactions is well known in the art. Protecting groups may be used for any functional group on any compound in any step of the process for synthesizing a final product, depending on the compatibility of the protecting groups with particular reagents, reaction conditions, and reaction sequences, as is known in the art.

EXAMPLE 1

Preparation of 2-(4-(4-cyclohexyloxazol-5-yl)phenyl)-1,1,1-trifluoro-propan-2-ol 4-(1,1,1-Trifluoro-2-hydroxypropan-2-yl)benzaldehyde

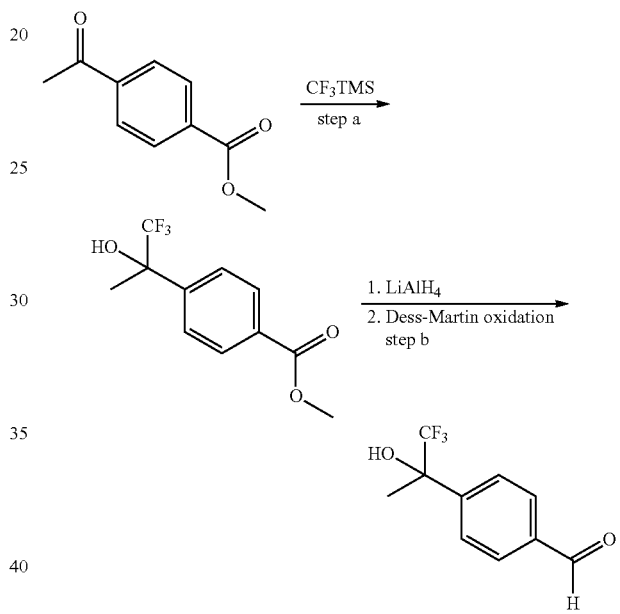

(a) To a mixture of methyl 4-acetylbenzoate (8.9 g, 50.0 mmol, 1.0 equiv.) and $CF_3SiMe_3$ (14.2 g, 100.0 mmol, 2.0 equiv.) in THF (100 mL) was added TBAF (75 mL, 1.0 M solution in THF, 75.0 mmol, 1.5 equiv.) dropwise at 0° C. After being stirred at r.t. for 12 h, the mixture was diluted with $CH_2Cl_2$ (100 mL). The organic layer was washed with saturated aqueous $NaHCO_3$ and brine, dried and concentrated in vacuo. The residue was purified by flash column chromatography (15% EtOAc/hexane) to give the ester as a colorless liquid: $^1H$ NMR (400 MHz, $CDCl_3$) δ 8.07 (d, J=8.5 Hz, 2 H), 7.67 (d, J=8.5 Hz, 2 H), 3.93 (s, 3 H), 2.70 (br, 1H), 1.80 (s, 3H); MS (ESI) 249.1 (M+H)$^+$.

(b)(1) To a solution of the ester obtained above (7.44 g, 30 mmol, 1.0 equiv.) in dry THF (50 mL) was slowly added $LiAlH_4$ (36 mL, 1.0 M solution in $Et_2O$, 36 mmol, 1.2 equiv.) at 0° C. After being stirred for 4 h at 0° C., the reaction mixture was quenched ($H_2O$ and 2N NaOH), extracted (EtOAc), dried ($Na_2SO_4$) and concentrated in vacuo. The crude material was purified by flash column chromatography (40% EtOAc/hexane) to provide the primary alcohol.

(2) The Dess-Martin periodinane (7.86 g, 18.5 mmol, 1.2 equiv.) was added to a solution of the alcohol obtained above (3.4 g, 15.5 mmol, 1.0 equiv.) in $CH_2Cl_2$ (10 mL) and THF (5 mL) at 0° C. After being stirred at r.t. for 24 h, the mixture was quenched with saturated aqueous NaHCO₃ and diluted with CH₂Cl₂. The aqueous layer was extracted with CH₂Cl₂, and the combined organic layers were washed with NaCl, dried with sodium sulfate, filtered and concentrated in vacuo. The crude material was purified by flash column chromatography (20% EtOAc/hexanes) to afford the aldehyde as a white solid: ¹H NMR (400 MHz, CDCl₃) δ 10.3 (s, 1 H), 8.00 (d, J=6.0 Hz, 12 H), 7.87 (d, J=6.0 Hz, 1 H), 2.85 (s, 1 H), 1.92 (s, 3 H).

2-(4-(4-Cyclohexyloxazol-5-yl)phenyl)-1,1,1-trifluoropropan-2-ol

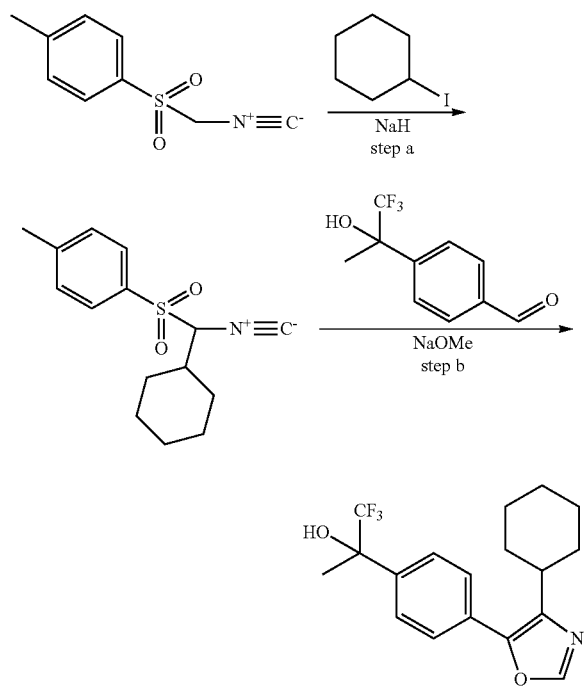

(a) NaH (0.8 g, 20.0 mmol, 60% dispersion in oil, 2.0 equiv.) was added to a solution of toluenesulphonylmethyl isocyanide (1.95 g, 10.0 mmol, 1.0 equiv.) in DMSO (10 mL) and Et₂O (10 mL) over 5 minutes at 0° C. and the reaction mixture was stirred while warming to r.t. for 20 minutes. Cyclohexyl iodide (1.55 mL, 12 mmol, 1.2 equiv) was added dropwise over 3 minutes and the resulting mixture was stirred at r.t. for 2 h. The reaction mixture was then diluted with ethyl acetate (250 mL), and the separated organic layer was washed with water (60 mL), dried over MgSO₄, filtered and concentrated under reduced pressure. The residue was purified by flash chromatography (20% EtOAc/hexane) to give the product as a white solid: ¹H NMR (400 MHz, CDCl₃) δ 7.88 (d, J=8.3 Hz, 2 H), 7.43 (d, J=8.3 Hz, 2 H), 4.30 (d, J=3.5 Hz, 1 H), 2.50 (s, 3 H), 2.42 (m, 1 H), 2.15 (1 H), 1.85-1.71 (m, 4 H), 1.44-1.19 (m, 5 H).

(b) The alkylated TosMIC obtained above (480 mg, 1.73 mmol, 1.2 equiv.) was dissolved in MeOH (2 mL) and treated with sodium methoxide (25% solution in MeOH, 0.94 mL, 3 equiv.), and 4-(1,1,1-trifluoro-2-hydroxypropan-2-yl)benzaldehyde (314 mg, 1.44 mmol, 1.0 equiv.) was then added. After being heated at 80° C. for 2 h, the reaction mixture was then cooled to r.t., diluted with ethyl acetate (80 mL) and washed with brine. The separated organic layer was dried over Na₂SO₄, filtered and concentrated under reduced pressure. The residue was purified by flash chromatography (30% EtOAc/hexane) to provide 2-(4-(4-cyclohexyloxazol-5-yl)phenyl)-1,1,1-trifluoropropan-2-ol as a white solid: ¹H NMR (400 MHz, CDCl₃) δ 7.85 (s, 1 H), 7.70 (d, J=8.4 Hz, 2 H), 7.62 (d, J=8.4 Hz, 2 H), 2.90 (m, 1 H), 2.88 (s, 1 H), 1.90 (m, 4 H), 1.84 (s, 3 H), 1.76 (m, 3 H), 1.36 (m, 3 H).

EXAMPLE 2

Preparation of 1,1,1-trifluoro-2-(4-(4-(1-tosylpiperidin-4-yl)oxazol-5-yl)phenyl)propan-2-ol 4-Bromo-1-tosylpiperidine

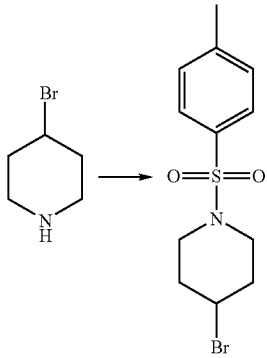 [SMILES: BrC1CCNCC1 ; Cc1ccc(S(=O)(=O)N2CCC(Br)CC2)cc1]

4-Bromopiperidine (5.75 g, 23.5 mmol) was dissolved in pyridine (50 mL) and treated with tosyl chloride (5.8 g, 30.5 mmol). The reaction mixture was stirred for 12 h at r.t. and then diluted with dichloromethane (150 mL) and HCl (1 M aqueous solution, 50 mL). The organic layer was washed with brine (80 mL), dried over MgSO₄, filtered and concentrated under reduced pressure. The residue was purified by flash chromatography (40% EtOAc/hexane) to give 4-bromo-1-tosylpiperidine as a white solid: ¹H NMR (400 MHz, CDCl₃) δ 7.66 (d, J=8.2 Hz, 2H), 7.34 (d, J=8.2 Hz, 2H), 4.27-4.24 (m, 1H), 3.20-3.17 (m, 2H), 3.13-3.11 (m, 2H), 2.46 (s, 3H), 2.23-2.17 (m, 2H), 2.08-2.05 (m, 2H); MS (ESI) 318.0 (M+H)⁺.

4-(Isocyano(tosyl)methyl)-1-tosylpiperidine

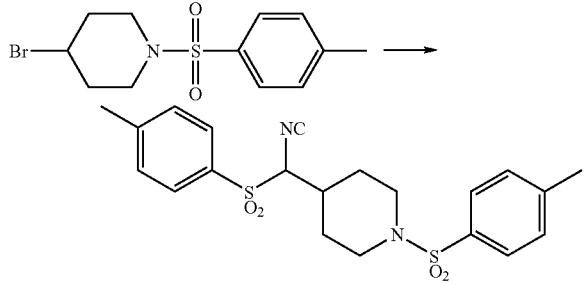

NaH (0.92 g, 23.07 mmol, 60% dispersion in oil) was added to DMF (70 mL) in one portion at 0° C. Toluenesulphonylmethyl isocyanide (3.0 g, 15.38 mmol) in DMF (12 mL) was added dropwise over 5 minutes and the mixture was stirred while warming to r.t. for 20 minutes. 4-Bromo-1-tosylpiperidine (4.46 g, 18.4 mmol) in DMF (10 mL) was then added dropwise over 3 minutes and the resulting mixture was stirred at r.t. for 16 h. The mixture was then diluted with ethyl acetate (250 mL) and LiCl (1 M aqueous solution, 60 mL), and the separated organic layer was washed with water (60 mL), dried over MgSO$_4$, filtered and concentrated under reduced pressure. The residue was purified by flash chromatography (20% EtOAc/hexane) to provide 4-(isocyano(tosyl)methyl)-1-tosylpiperidine as a white solid: $^1$H NMR (400 MHz, CDCl$_3$) δ 7.79 (d, J=8.0 Hz, 2H), 7.61 (d, J=7.6 Hz, 2H), 7.38 (d, J=8.0 Hz, 2H), 7.32 (d, J=7.6 Hz, 2H), 4.34 (d, J=4.0 Hz, 1H), 3.87-3.84 (m, 2H), 2.44 (s, 3H), 2.43 (s, 3H), 2.30-2.10 (m, 2H), 2.10-2.0 (m, 1H), 2.0-1.70 (m, 4H); MS (ESI) 451.1 (M+H+H$_2$O)$^+$.

1,1,1-Trifluoro-2-(4-(4-(1-tosylpiperidin-4-yl)oxazol-5-yl)phenyl)propan-2-ol

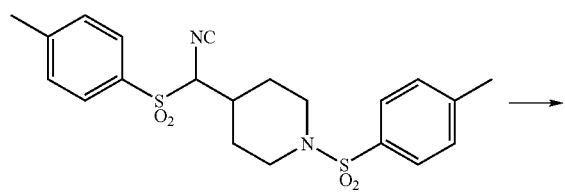

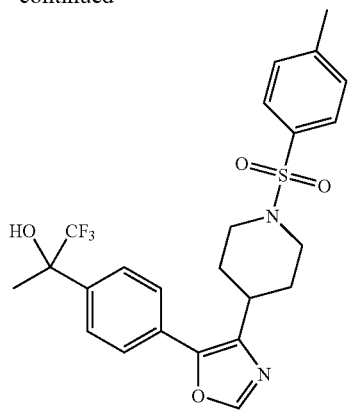

4-(Isocyano(tosyl)methyl)-1-tosylpiperidine (260 mg, 0.73 mmol) was dissolved in MeOH (6 mL) and treated with sodium methoxide (1.0 M solution in MeOH, 0.7 mL), and 4-(1,1,1-trifluoro-2-hydroxypropan-2-yl)benzaldehyde (159 mg, 0.73 mmol) was then added. After being stirred at 80° C. for 2 h, the mixture was then cooled to r.t. and diluted with ethyl acetate (80 mL) and saturated aqueous NaHCO$_3$ (30 mL). The separated organic layer was dried over MgSO$_4$, filtered and concentrated under reduced pressure. The residue was purified by flash chromatography (15% EtOAc/hexane) to provide 1,1,1-trifluoro-2-(4-(4-(1-tosylpiperidin-4-yl)oxazol-5-yl)phenyl)propan-2-ol as a white solid: $^1$H NMR (400 MHz, CDCl$_3$) δ 7.83 (s, 1H), 7.69-7.65 (m, 2H), 7.51-7.49 (m, 2H), 7.36-7.33 (m, 4H), 3.90 (d, J=11.7 Hz, 2H), 3.30-3.28 (s, 1H), 2.79 (tt, J=3.9 Hz, 11.7 Hz, 1H), 2.45 (s, 3H), 2.37 (td, J=2.3 Hz, 12.1 Hz, 2H), 2.17-2.07 (m, 2H), 1.85 (d, J=12.1 Hz, 2H), 1.80 (s, 3H); MS (ESI) 495.1 (M+H)$^+$.

EXAMPLE 3

Preparation of 2-(4-(4-cyclohexylisoxazol-5-yl)phenyl)-1,1,1-trifluoropropan-2-ol

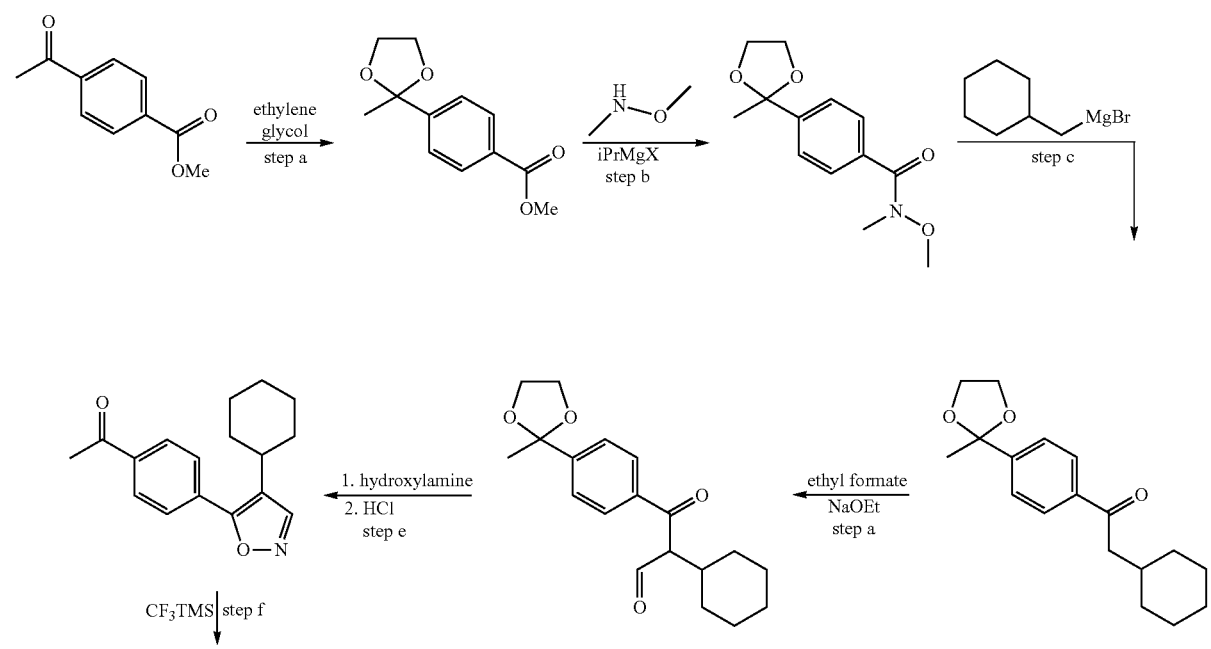

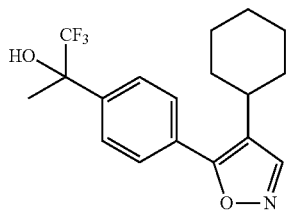

(a) Methyl 4-acetylbenzoate (20.0 g, 112.3 mmol) was dissolved in benzene (250 mL), and ethylene glycol (6.3 mL, 112.3 mmol) and para-toluenesulfonic acid (1.92 g, 11.2 mmol) were added in one portion. After being heated at reflux for 3 h using a Dean-Stark trap, the mixture was then allowed to cool and washed successively with saturated aqueous NaHCO$_3$, water and brine. The separated organic layer was dried over MgSO$_4$, filtered and concentrated under reduced pressure. The residue was purified by flash chromatography (15% EtOAc/hexane) to give the ketal as a colorless oil: $^1$H NMR (400 MHz, CDCl$_3$) δ 7.98 (d, J=8.6 Hz, 2H), 7.53 (d, J=8.6 Hz, 2H), 4.04-4.01 (m, 2H), 3.88 (s, 3H), 3.75-3.71 (m, 2H), 1.62 (s, 3H); (ESI) 223.1 (M+H)$^+$.

(b) The ketal obtained above (18.5 g, 83.3 mmol) was slurried with N,O-dimethylhydroxylamine hydrochloride (10.15 g, 104.1 mmol) in anhydrous THF (150 mL) and cooled to $^-$10° C. Isopropyl magnesium chloride (125 mL, 2.0 M solution in THF, 250 mmol) was added dropwise via an addition funnel over 20 min. The mixture was allowed to warm to r.t. and stirred for 2 hours and then quenched with saturated aqueous NH$_4$Cl (100 mL), water (60 mL) and diluted with ethyl acetate (80 mL). The separated aqueous layer was extracted with ethyl acetate (300 mL), dried over MgSO$_4$, filtered and concentrated under reduced pressure. The residue was purified by flash chromatography (20% EtOAc/hexane) to provide the benzamide as a colorless oil: $^1$H NMR (400 MHz, CDCl$_3$) δ 7.66 (d, J=8.6 Hz, 2H), 7.53 (d, J=8.6 Hz, 2H), 4.08-4.06 (m, 2H), 3.80-3.78 (s, 2H), 3.59 (s, 3H), 3.38 (s, 3H), 1.67 (s, 3H), MS (ESI) 252.1 (M+H)$^+$.

(c) (Bromomethyl)cyclohexane (8.3 mL, 60 mmol) was added to a mixture of Mg (1.44 g, 60 mmol) and I$_2$ (10 mg) in anhydrous THF (100 mL) at r.t. under a N$_2$ atmosphere. The mixture was stirred for 2 hours and then added to a solution of the benzamide obtained above (5.0 g, 20 mmol) in anhydrous THF (80 mL). The resulting reaction mixture was stirred for 2 hours at r.t. and then diluted with ethyl acetate (300 mL), saturated aqueous NH$_4$Cl (60 mL) and water (140 mL). The separated organic layer was dried over MgSO$_4$, filtered and concentrated under reduced pressure. The residue was purified by flash chromatography (15% EtOAc/hexane) to give the ketone as a white solid: $^1$H NMR (400 MHz, CDCl$_3$) δ 8.57 (s, 1H), 7.61 (dd, 1H, J=7.0 Hz, 7.0 Hz, 1H), 7.31 (d, J=8.0 Hz, 1H), 7.11 (dd, J=5.4 Hz, 5.4 Hz, 1H), 4.58 (s, 2H); 4.41 (s, 2H), 2.69-2.67 (m, 1H), 2.13-2.06 (m, 3H), 1.90-1.60 (m, 6H), 1.49-1.46 (m, 2H), 0.44-0.33 (m, 4H); MS (ESI) 289.1 (M+H)$^+$.

(d) The ketone obtained above (1.6 g, 5.55 mmol) was dissolved in ethyl formate (20 mL), and sodium ethoxide (755 mg, 11.1 mmol) was added in one portion. The reaction mixture was stirred for 16 h at r.t. and then diluted with ethyl acetate (250 mL) and saturated aqueous NaHCO$_3$ (100 mL). The separated organic layer was dried over MgSO$_4$, filtered and concentrated under reduced pressure. The residue was purified by flash chromatography (10% EtOAc/hexane) to provide the ketoaldehyde as a colorless oil: $^1$H NMR (400 MHz, CDCl$_3$) δ 9.60 (d, J=4.7 Hz, 1H), 7.88 (d, J=8.2 Hz, 2H), 7.54 (d, J=8.2 Hz, 2H), 4.10 (dd, J=4.7 Hz, 9.4 Hz, 1H), 4.00-3.97 (m, 2H), 3.73-3.67 (m, 2H), 2.40-2.31 (m, 1H), 1.69-1.57 (m, 5H), 1.57 (s, 3H), 1.21-0.95 (m, 5 H); MS (ESI) 317.2 (M+H)$^+$.

(e) Hydroxylamine hydrochloride (48.4 mg, 0.71 mmol) was added to a solution of the ketoaldehyde obtained above (150 mg, 0.48 mmol) in pyridine (1 mL). After being heated at 80° C. for 1 h, the mixture was cooled to 23° C. and quenched with 3 N HCl. The aqueous layer was extracted with EtOAc, and the combined organic layers were washed with NaCl, dried with sodium sulfate, filtered and concentrated in vacuo. The crude material was dissolved in THF (2 mL) and conc. HCl (0.5 mL) and stirred for 1 h. The reaction mixture was quenched with saturated aqueous NaHCO$_3$ and diluted with CH$_2$Cl$_2$. The aqueous layer was extracted with EtOAc, and the combined organic layers were washed with NaCl, dried with sodium sulfate, filtered and concentrated in vacuo. The crude material was purified by flash column chromatography (20% EtOAc/hexanes) to afford the ketoisoxazole as a white solid.

(f) To a solution of the ketoisoxazole obtained above (80 mg, 0.26 mmol) and CF$_3$TMS (72.7 mg, 0.52 mmol) in THF (1 mL) at 0° C. was added TBAF (383 μL, 1 M solution in THF, 0.38 mmol) dropwise. After being stirred at r.t. for 12 h, the mixture was quenched with saturated aqueous NaHCO$_3$ and diluted with EtOAc. The aqueous layer was extracted with EtOAc, and the combined organic layers were washed with NaCl, dried with sodium sulfate, filtered and concentrated in vacuo. The crude material was purified by flash column chromatography (20% EtOAc/hexanes) to afford 2-(4-(4-cyclohexylisoxazol-5-yl)phenyl)-1,1,1-trifluoropropan-2-ol as a white solid: $^1$H NMR (400 MHz, CDCl$_3$) δ 8.26 (s, 1 H), 7.75 (m, 4 H), 2.79 (m, 1 H), 2.71 (s, 1 H), 1.95-1.78 (m, 6 H), 1.85 (s, 3 H), 1.46-1.28 (m, 4 H).

EXAMPLE 4

Preparation of 2-(4-(4-cyclohexylisoxazol-5-yl)phenyl)propan-2-ol

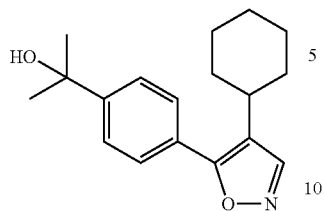

Methyl lithium (159 μL, 1.6 M solution in Et₂O, 0.25 mmol) was added dropwise to a solution of 1-(4-(4-cyclohexylisoxazol-5-yl)phenyl)ethanone obtained above (57 mg, 0.21 mmol) in THF (2 mL) at 0° C. After stirring for 15 min, another 100μL of the methyl lithium solution was added to the reaction mixture. After being stirred for an additional 1 h at 0° C., the mixture was quenched with saturated aqueous NH₄Cl and diluted with EtOAc. The aqueous layer was extracted with EtOAc, and the combined organic layers were washed with NaCl, dried with magnesium sulfate, filtered and concentrated in vacuo to give a yellow oil. The crude material was purified by flash column chromatography (20%→40% EtOAc/hexanes) to afford 2-(4-(4-cyclohexylisoxazol-5-yl)phenyl)propan-2-ol as a colorless oil: ¹H NMR (400 MHz, CDCl₃) δ 8.23 (s, 1H), 7.62 (m, 4H), 2.77 (m, 1H), 2.09 (m, 1H), 1.86 (m, 5H), 1.63 (s, 6H), 1.37 (m, 5H).

EXAMPLE 5

Preparation of 2-(4-(4-cyclohexyl-3-methylisoxazol-5-yl)phenyl)-1,1,1-trifluoropropan-2-ol

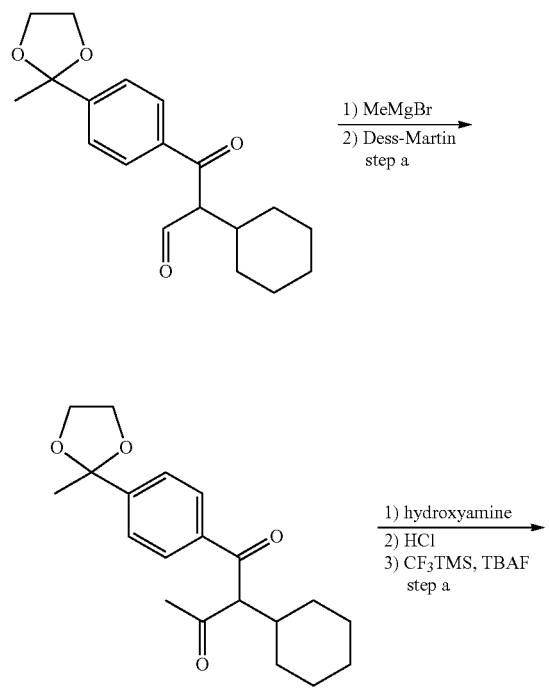

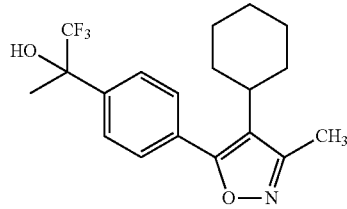

(a)(1) Methylmagnesium bromide (830 μL, 3 M solution in Et₂O, 2.5 mmol) was added dropwise to a solution of the ketoaldehyde obtained above (395 mg, 1.25 mmol) in Et₂O (3 mL) at 0° C. After approximately half of the Grignard reagent had been added, 2 mL of THF was added and the reaction mixture was warmed to 23° C., at which point the remaining Grignard reagent was added. After being stirred for 30 min, the mixture was quenched with saturated aqueous NH₄Cl and diluted with EtOAc. The aqueous layer was extracted with EtOAc, and the combined organic layers were washed with NaCl, dried with magnesium sulfate, filtered and concentrated in vacuo to give a yellow oil. The crude material was purified by flash column chromatography (5% →25% EtOAc/hexanes) to afford the alcohol as colorless oil.

(2) The Dess-Martin periodinane (257 mg, 0.60 mmol) was added to a mixture of the alcohol obtained above (134 mg, 0.40 mmol) and sodium bicarbonate (67 mg, 0.80 mmol) in CH₂Cl₂ (10 mL) at 0° C. After being stirred for 2 h, the mixture was quenched with saturated aqueous NaHCO₃ and diluted with CH₂Cl₂. The aqueous layer was extracted with CH₂Cl₂, and the combined organic layers were washed with NaCl, dried with magnesium sulfate, filtered and concentrated in vacuo to give a yellow oil. The crude material was purified by flash column chromatography (15% →25% EtOAc/hexanes) to afford the diketone as a colorless oil.

(b)(1) Hydroxylamine hydrochloride (50 mg, 0.72 mmol) was added to a solution of the diketone obtained above (118 mg, 0.36 mmol) in pyridine (4 mL) and the resulting mixture was heated to 80° C. After being stirred for 19 h, the mixture was cooled to 23° C. and quenched with 3 N HCl. The aqueous layer was extracted with EtOAc, and the combined organic layers were washed with NaCl, dried with magnesium sulfate, filtered and concentrated in vacuo to afford the crude oxime.

(2) The crude oxime was dissolved in THF (2 mL), 2 N HCl (1 mL) was added, and the solution was stirred for 4 h. The reaction mixture was quenched with saturated aqueous NaHCO₃ and diluted with CH₂Cl₂. The aqueous layer was extracted with CH₂Cl₂, and the combined organic layers were washed with NaCl, dried with magnesium sulfate, filtered and concentrated in vacuo. The crude material was purified by flash column chromatography (8% →25% EtOAc/hexanes) to afford the ketoisoxazole as a white solid.

(3) To a solution of the ketoisoxazole obtained above (66 mg, 0.23 mmol) and CF₃TMS (45 μL, 0.30 mmol) in THF (1 mL) at 0° C. was added TBAF (340 μL, 1 M solution in THF, 0.34 mmol) dropwise. After being stirred for 1 h, the mixture was quenched with saturated aqueous NaHCO₃ and diluted with CH₂Cl₂. The aqueous layer was extracted with CH₂Cl₂, and the combined organic layers were washed with NaCl, dried with magnesium sulfate, filtered and concentrated in vacuo. The crude material was purified by flash column chromatography (15% →30% EtOAc/hexanes) to furnish the title alcohol as a white foam: ¹H NMR (400 MHz, CD₃OD) δ 7.80 (d, J=8.3 Hz, 2H), 7.59 (m, 2H), 2.76 (tt, J=12.2, 3.5 Hz, 1H), 2.41 (s, 3H), 1.79 (s, 3H), 1.76 (m, 7H), 1.35 (m, 3H); anal. calcd for C₁₉H₂₂F₃NO₂: C, 64.58; H, 6.28; N, 3.96. found: C, 64.49; H, 6.27; N, 3.93.

EXAMPLE 6

Preparation of 2-(4-(4-cyclohexylisoxazol-3-yl)phenyl)propan-2-ol

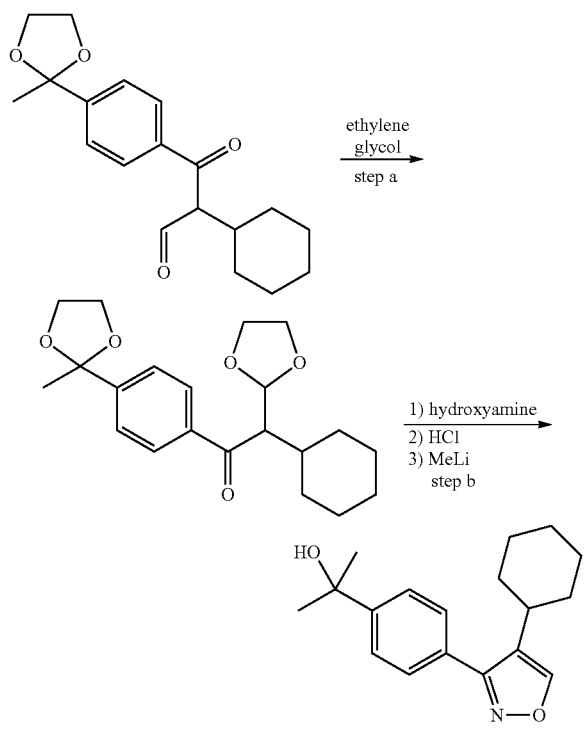

(a) The ketoaldehyde obtained above (0.17 g, 0.54 mmol) was dissolved in benzene (5 mL) and treated with ethylene glycol (0.03 mL, 0.54 mmol) and para-toluenesulfonic acid (9 mg, 0.054 mmol). After being heated at 80° C. for 12 h, the mixture was cooled to r.t. and diluted with ethyl acetate (60 mL) and saturated aqueous NaHCO₃ (30 mL). The separated organic layer was dried over MgSO₄, filtered and concentrated under reduced pressure. The residue was purified by flash chromatography (10% EtOAc/hexane) to give the acetal as a colorless oil: $^1$H NMR (400 MHz, CDCl₃) δ 7.88 (d, J=8.6 Hz, 2H), 7.54 (d, J=8.2 Hz, 2H), 5.25 (d, J=7.0 Hz, 1H), 4.06-4.02 (m, 2H), 3.94-3.74 (m, 6H), 3.55 (dd, J=7.0 Hz, 7.0 Hz, 1H), 2.03-1.94 (m, 2H), 1.73-1.59 (m, 4H), 1.64 (s, 3H), 1.26-1.03 (m, 5 H); LC MS (ESI) 361.1 (M+H)⁺.

(b)(1) The acetal (320 mg, 0.89 mmol) was dissolved in pyridine (5 mL) and treated with hydroxylamine hydrochloride (200 mg, 2.89 mmol). After being heated at 100° C. for 16 h, the reaction mixture was then cooled to r.t. and diluted with ethyl acetate (100 mL) and water (50 mL). The separated organic layer was dried (MgSO4), filtered and concentrated under reduced pressure to provide the crude oxime.

(2) The crude oxime was dissolved in anhydrous THF (5 mL) and treated with conc. HCl (0.5 mL). The resulting mixture was stirred at r.t. for 14 h and then diluted with ethylacetate (100 mL) and saturated aqueous NaHCO₃ (50 mL). The separated organic layer was dried over MgSO₄, filtered and concentrated under reduce pressure. The residue was purified by flash chromatography (5% EtOAc/hexane) to afford the reverse ketoisoxazole as a white solid: $^1$H NMR (400 MHz, CDCl₃) δ 8.26 (s, 1H), 8.06 (d, J=5.8 Hz, 2H), 7.72 (d, J=5.8 Hz, 2H), 2.66 (s, 3H), 2.65-2.62 (m, 1H), 1.92-1.89 (m, 2H), 1.76-1.60 (m, 3H), 1.30-1.22 (m, 5H); MS (ESI) 270.1 (M+H)⁺.

(3) The reverse ketoisoxazole (140 mg, 0.52 mmol) was dissolved in anhydrous THF (10 mL) and cooled to 0° C. The reaction mixture was treated with methyl lithium (1.6 M solution in THF, 0.62 mL, 1.04 mmol) and stirred for 2.5 h at r.t. The reaction was then diluted with ethyl acetate (60 mL) and water (30 mL), and the separated organic layer was dried over MgSO₄, filtered and concentrated under reduced pressure. The residue was purified by flash chromatography (10% EtOAc/hexane) to provide 2-(4-(4-cyclohexylisoxazol-3-yl)phenyl)propan-2-ol as a white solid: $^1$H NMR (400 MHz, CDCl₃) δ 8.23 (s, 1H), 7.60 (s, 4H), 2.61-2-56 (m, 1H), 1.93-1.89 (m, 2H), 1.76-1.62 (m, 3H), 1.63 (s, 6H), 1.30-1.22 (m, 5H); MS (ESI) 286.1 (M+H)⁺.

EXAMPLE 7

Preparation of 2-(4-(5-cyclohexyl-2-methylthiazol-4-yl)phenyl)-1,1,1-trifluoropropan-2-ol

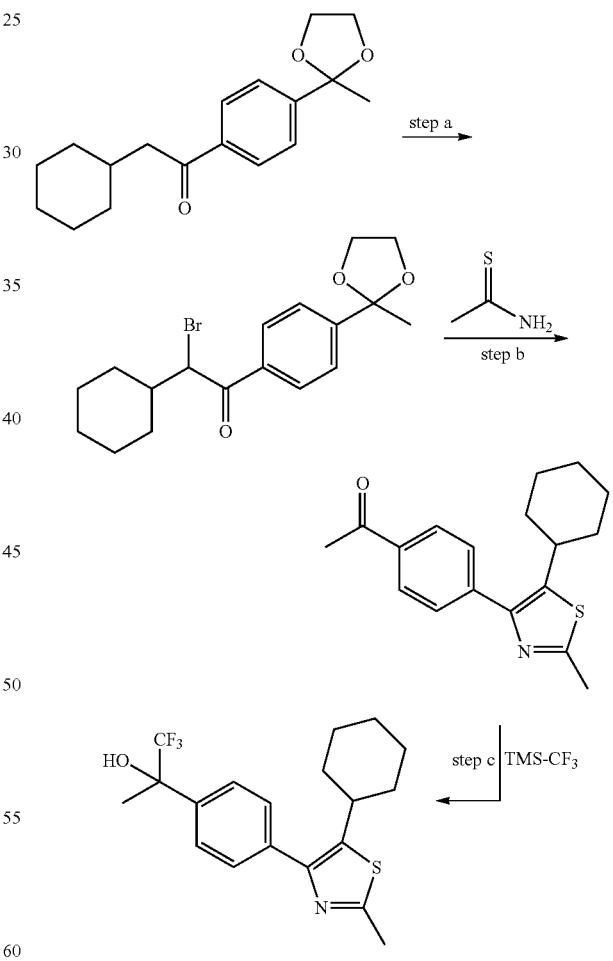

(a) To a solution of 2-cyclohexyl-1-(4-(2-methyl-1,3-dioxolan-2-yl)phenyl)ethanone obtained above (1.5 g, 5.2 mmol, 1.0 equiv.) in DCM (10 mL) was added pyridinium tribromide (1.66 g, 5.2 mmol, 1.0 equiv.). After being stirred at 25° C. for 3 h, the resulting mixture was diluted (sat. NaHCO₃) and extracted (10% MeOH/DCM). The organic layer was dried (Na$_2$SO$_4$) and concentrated under reduced pressure. Purification by flash chromatography (SiO$_2$, 5-9% EtOAc/hexane) gave the α-bromo ketone as a colorless oil.

(b) To a solution of thioacetamide (150 mg, 2.0 mmol, 1.0 equiv.) in MeOH (2 mL) was added a solution of the α-bromo ketone obtained above (740 mg, 2.0 mmol, 1.0 equiv.) in MeOH (2 mL) dropwise at 50° C. After being stirred at 50° C. for 4 h, the resulting mixture was diluted (sat. NaHCO$_3$) and extracted (10% MeOH/DCM). The organic layer was dried (Na$_2$SO$_4$) and concentrated under reduced pressure. Purification by flash chromatography (SiO$_2$, 5-20% EtOAc/hexane) gave the ketothiazole as a colorless oil.

(c) To a mixture of the ketothiazole (30 mg, 0.1 mmol, 1.0 equiv.) and TMS-CF$_3$ (21.3 mg, 0.15 mmol, 1.5 equiv.) in THF (1 mL) was added TBAF (1.0 M in THF, 0.2 mL, 0.2 mmol, 2.0 equiv.). After being stirred at 25° C. for 0.5 h, the resulting mixture was diluted (sat. NaHCO$_3$) and extracted (10% MeOH/DCM). The organic layer was dried (Na$_2$SO$_4$) and concentrated under reduced pressure. Purification by flash chromatography (SiO$_2$, 10-20% EtOAc/hexane) afforded the title alcohol as a white solid: $^1$H NMR (CDCl$_3$) δ 7.64 (d, J=8.2 Hz, 2 H), 7.57 (d, J=8.2 Hz, 2 H), 3.02 (m, 1 H), 2.86 (s, 1H), 2.71 (s, 3H), 2.02 (m, 2H), 1.84-1.74 (m, 5H), 1.75-1.47 (m, 6H).

BIOLOGICAL EXAMPLES

Procedures Useful for Biological Evaluation of Tricyclic Compounds

In addition to the extensive literature disclosing the role of HSDs in various diseases and disorders, described herein are assays useful for testing the tricyclic compounds of the present invention.

Assays

Inhibition of 11β-HSD1 (11β-Hydroxysteroid Dehydrogenase Type 1) Activity in vitro Inhibition of 11β-HSD1 activity was examined by quantitative determination, by an SPA (scintillation proximity assay) system, of the suppressive action on the conversion from cortisone to cortisol using human 11β-HSD1 (hereinafter recombinant 11β-HSD1) expressed using a baculo-virus system as an enzyme source. For the reaction, a reagent was added to a 96-well plate (96-well Opti-plates™-96 (Packard)) to the following final concentration and a volume of 100 µl, and the reaction transpired at room temperature for 90 min. The reaction solution used was 0.1 µg/ml recombinant 11β-HSD1, 500 µM NADPH, 16 nM $^3$H cortisone (Amersham Biosciences, 1.78 Tbq/mol) dissolved in 0.1% BSA (Sigma)-containing PBS and the test drug was 2 µl of a compound solution (dissolved in DMSO). After 90 min, the reaction was stopped by adding PBS (40 µl, containing 0.1% BSA (Sigma)) containing 0.08 µg of anti-cortisol mouse monoclonal antibody (East Coast Biologics), 365 µg SPA PVT mouse antibody-binding beads (Amersham Biosciences) and 175 µM carbenoxolone (Sigma) to the reaction solution. After completion of the reaction, the plate was incubated overnight at room temperature and the radioactivity was measured by Topcount (Packard). For control, the value (0% inhibition) of the well containing 2 µl of DMSO instead of the test drug was used, and for positive control, the value (100% inhibition) of the well containing carbenoxolone instead of the test drug at the final concentration of 50 µM was used. The inhibition (%) of the test drug was calculated by ((value of control−value of test drug)/(value of control−value of positive control))×100 (%). The IC$_{50}$ value was analyzed using a computer-based curve fitting software.

This example provides assays that are useful in evaluating and selecting a compound that modulates 11β-HSD1.

Biochemical 11β-HSD1 Assay by SPA

Recombinant human, mouse and rat 11β-HSD1 were expressed in baculovirus expression system, isolated by affinity purification and used as the enzyme sources for cortisone to cortisol conversion in vitro. $^3$H-Cortisone (Amersham Bioscience, 1.78 Tbq/mol. 49 Ci/mmol) was used as the substrate, and a monoclonal anti-cortisol antibody and the scintillation proximity assay (SPA) system were used to detect the product of the 11β-HSD1-catalyzed reaction, $^3$H-cortisol. Reactions took place at room temperature for 90 min. in 96-well Opti-plates™-96 (Packard) in 100 µL volume with 2 µL test compounds or control in DMSO, 0.1 µg/mL 11β-HSD1 protein, 500 µM NADPH and 16 nM radioactive cortisone, in PBS buffer supplemented with 0.1% BSA (Sigma). Reaction was stopped with the addition of 40 µL buffer containing 0.08 µg anti-cortisol monoclonal antibody (East Coast Biologics), 365 µg SPA PVT antibody-binding beads (Amersham Biosciences) and 175 µM carbenoxolone (Sigma).

Plates were incubated at room temperature overnight before being read on a Topcount (Packard). The point of 50% inhibition of 11β-HSD1 enzyme activity (IC$_{50}$) was determined by computer-based curve fitting.

Cell-Based 11β-HSD1 Assay by Spa

This cell-based assay measures the conversion of $^3$H-cortisone to $^3$H-cortisol in a HEK-293 cell line stably overexpressing human recombinant 11β-HSD1. HEK-293 cells were grown in DMEM/F12 supplemented with 10% fetal bovine serum, and plated onto poly-D-lysine-coated 96-well assay plates (Costar 3903), 100,000 cells per well in 50 µL assay media (phenol-free DMEM/F12 (Invitrogen)+0.2% BSA+1% antibiotic-antimycotic solutions). The solution was incubated at 37° C. for 24 h, and the reaction was initiated by the addition of 25 µL of assay media containing a compound of desired concentration and 25 µL of assay media containing 40 nM of $^3$H-cortisone to each well. The reaction mixture was incubated at 37° C. for 90 min. and the reaction terminated by the addition of 25 µL of assay media containing 0.2 µg of anti-cortisol monoclonal antibody (East Coast Biologics), 500 µg SPA PVT antibody-binding beads (Amersham Biosciences) and 500 µM carbenoxolone (Sigma).

Plates were incubated at room temperature for at least 2 h before being read on Topcount (Packard). The point of 50% inhibition of 11β-HSD1 enzyme activity (IC$_{50}$) was determined by computer-based curve fitting.

Scintillation Proximity Assay (SPA)

[1,2(n)-$^3$H]-cortisone was purchased from Amersham Pharmacia Biotech. Anti-cortisol monoclonal mouse antibody, clone 6D6.7, was obtained from Immunotech, and Scintillation Proximity Assay (SPA) beads coated with monoclonal antimouse antibodies were purchased from Amersham Pharmacia Biotech. NADPH, tetrasodium salt was obtained from Calbiochem, and glucose-6-phosphate (G-6-P) was supplied by Sigma. The human 11-β-hydroxysteroid dehydrogenase type 1 enzyme (11-β-HSD1) was expressed in *Pichia pastoris*. 18-β-glycyrrhetinic acid (GA) was obtained from Sigma. The serial dilutions of the compounds were performed on a Tecan Genesis RSP 150. Compounds to be tested were dissolved in DMSO (1 mM) and diluted in 50 mM Tris-HCl, pH 7.2, containing 1 mM EDTA.

The multiplication of plates was done on a WallacQuadra. The amount of the product [³H]-cortisol bound to the beads was determined in a Packard, Top Count microplate liquid scintillation counter.

The 11-β-HSD1 enzyme assay was carried out in 96-well microtiter plates (Packard, Optiplate) in a total well volume of 220 µL and contained 30 mM Tris-HCl, pH 7.2, with 1 mM EDTA, a substrate mixture tritiated Cortisone/NADPH (175 nM/181 µM), G-6-P (1 mM) and inhibitors in serial dilutions (9 to 0.15 µM). Reactions were initiated by the addition of human 11-β-HSD1, either as *Pichia pastoris* cell homogenate or microsomes prepared from *Pichia pastoris* (the final amount of enzyme used was varied between 0.057 to 0.11 mg/mL). Following mixing, the plates were shaken for 30 to 45 minutes at room temperature. The reactions were terminated with 10 µL 1 mM GA stop solution. Monoclonal mouse antibody was then added (10 µL of 4 µM) followed by 100 µL of SPA beads (suspended according to the manufacturers instructions). Appropriate controls were set up by omitting the 11-β-HSD1 to obtain the non-specific binding (NSB) value.

The plates were covered with plastic film and incubated on a shaker for 30 minutes, at room temperature, before counting. The amount of [³H]-cortisol bound to the beads was determined in a microplate liquid scintillation counter. The calculation of the $K_i$ values for the inhibitors was performed by use of Activity Base. The $K_i$ value is calculated from $IC_{50}$ and the $K_m$ value is calculated using the Cheng Prushoff equation (with reversible inhibition that follows the Michaelis-Menten equation): $K_i=IC_{50}(1+[S]/K_m)$ (Cheng, Y. C.; Prushoff, W. H., Biochem. Pharmacol. 1973, 22, 3099-3108). The $IC_{50}$ is measured experimentally in an assay wherein the decrease of the turnover of cortisone to cortisol is dependent on the inhibition potential of each substance.

Cloning, Expression and Purification of 11β-HSD1

The expression and purification of the murine enzyme is described by J. Zhang et al., Biochemistry 2005, 44, 6948-57. The expression and purification of the human enzyme is similar to that of the murine sequence.

Enzyme Assay

The $IC_{50}$ and $K_i$ of the compounds are determined by the following method:

1. Prepare an Assay Buffer, (pH 7.2, 50 mM Tris-HCL, 1 mM EDTA) fresh each week.
2. Prepare the following solutions:
NADPH (Sigma, 200 µM)
³H-Cortisone (Amersham Biosciences, 45 Ci/mmol, 200 nM)
Enzyme Prep (20 nM for human, 10 nM for mouse)
Cortisol Antibody (East Coast Biologicals, 1:50 dilution)
Anti-mouse SPA beads (Amersham Biosciences, 15 mg/ml)
18β-Glycyrrhetinic acid ("GA") (Aldrich, 1 µM)
Compound Stock Solution (10 mM in DMSO), serially diluted in Assay Buffer. Each compound is normally tested at six different concentrations (10 µM to 0.1 nM). All of the solutions and dilutions are made in the Assay Buffer.
3. Assay is run using white/white, 96-well assay plates (Corning) in a total volume of 100 µL.
4. Into each well of a 96-well plate is added Assay Buffer (30 µL), compound (10 µL), NADPH (10 µL), and ³H-cortisone (10 µL).
5. Initiate reaction by adding 40 µL of HSD-1 enzyme prep to the wells.
6. The plate is covered with tape and incubated on an orbital shaker for 1 h at room temperature.
7. After 1 h, the tape is removed and anti-cortisol antibody (10 µL), GA solution (10 µL and SPA bead preparation (100 µL) are added.
8. The plate is incubated (30 min) on an orbital shaker at room temperature.
9. The counts are read on a TopCount NXT reader.
10. A dose-response curve is first plotted using the Graphpad Prism software to generate the $IC_{50}$ values.
11. With the $IC_{50}$ value and the known $K_m$ value for the substrate and HSD1 enzyme, an estimated $K_i$ can be calculated with the Chen and Prusoff equation $\{K_i=IC_{50}/[1+(\text{substrate}/K_m)]\}$.

The compounds of the present invention show inhibitory activity against the 11β-HSD1 enzyme in the assays, with $IC_{50}$ values ranging from 55 nM to 1000 nM.

We claim:

1. A compound selected from the group consisting of:

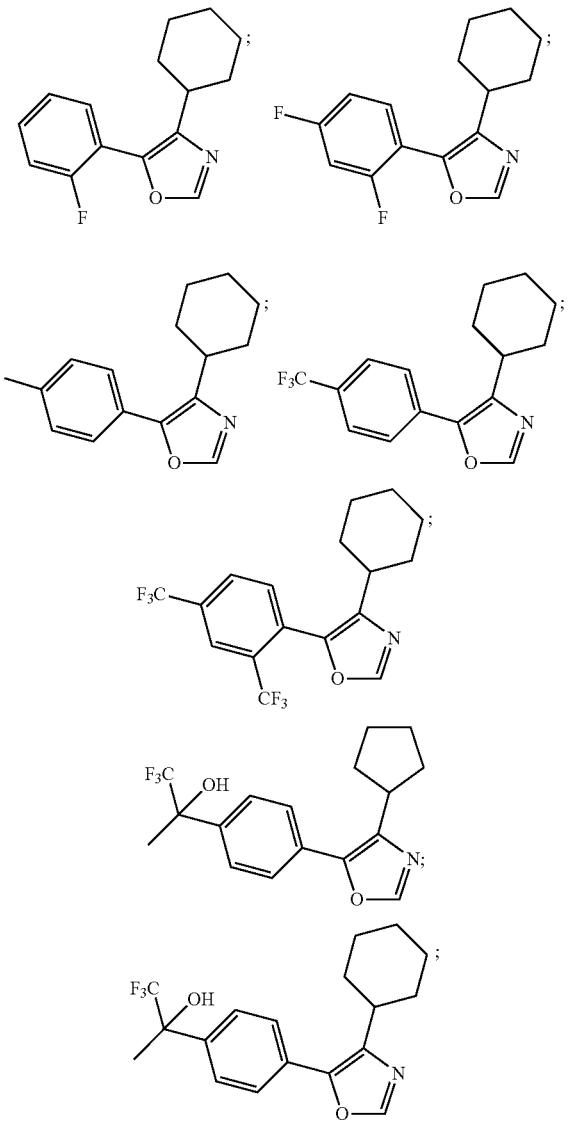

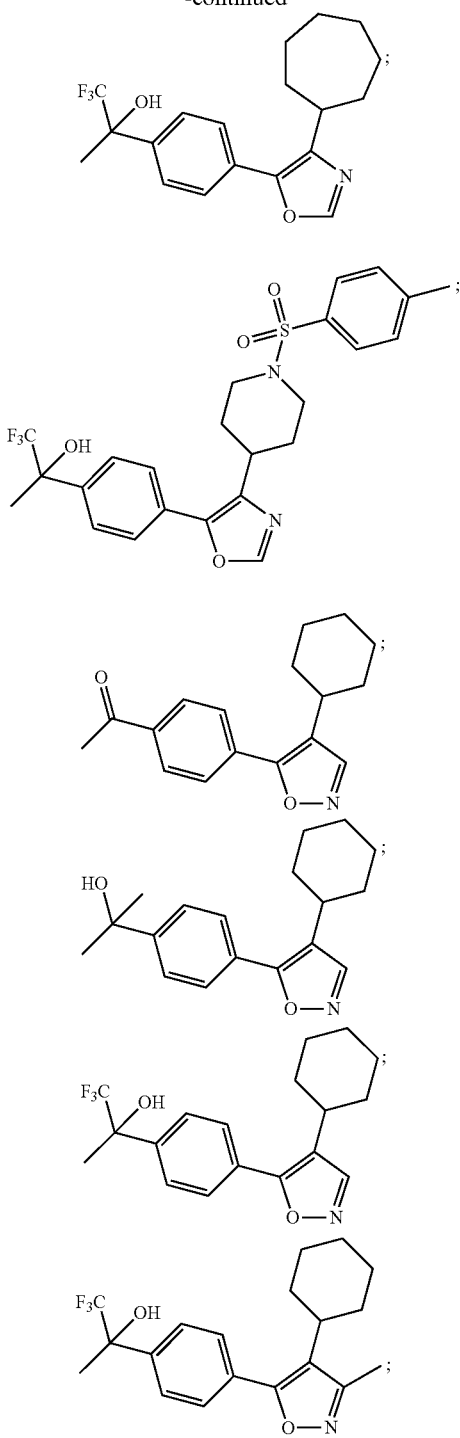

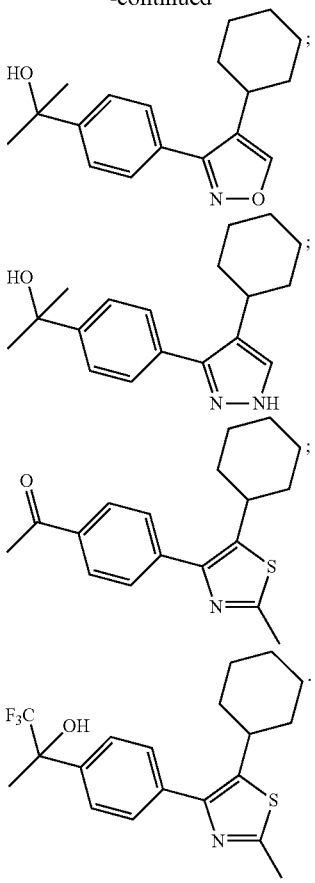

2. A pharmaceutical composition comprising a therapeutically effective amount of a compound according to claim 1, and a pharmaceutically acceptable carrier.

3. A pharmaceutical composition comprising a therapeutically effective amount of a compound according to claim 1, and one or more additional therapeutic agents.

4. The pharmaceutical composition according to claim 3, wherein the one or more additional therapeutic agents are useful for treating a condition or disorder selected from the group consisting of diabetes, syndrome X, obesity, polycystic ovarian disease, an eating disorder, craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia, Cushing's syndrome, hypertension, atherosclerosis, vascular restenosis, retinopathy, nephropathy, neurodegenerative disease, neuropathy, muscle wasting, a cognitive disorder, dementia, depression, psoriasis, glaucoma, osteoporosis, a viral infection, an inflammatory disorder, and an immune disorder.

* * * * *